US012718922B2

(12) United States Patent
Nieten et al.

(10) Patent No.: US 12,718,922 B2
(45) Date of Patent: Aug. 25, 2026

(54) COMPUTERIZED FULFILLMENT DEVICE WITH AUTOMATED PRIORITIZATION ENGINE

(71) Applicant: Express Scripts Strategic Development, Inc., St. Louis, MO (US)

(72) Inventors: Daniel A. Nieten, Chuluota, FL (US); Yarong Xu, Woodinville, WA (US); Jessica E. Chisholm, St. Louis, MO (US); Lee J. Morris, Columbus, OH (US); Peter A. Rosomoff, Wildwood, MO (US); Patricia M. Korando, St. Peters, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 1218 days.

(21) Appl. No.: 17/497,066

(22) Filed: Oct. 8, 2021

(65) Prior Publication Data

US 2022/0115105 A1 Apr. 14, 2022

Related U.S. Application Data

(63) Continuation-in-part of application No. 16/731,690, filed on Dec. 31, 2019, now Pat. No. 11,232,399, and (Continued)

(51) Int. Cl.
*G16H 20/13* (2018.01)
*G06N 20/00* (2019.01)

(Continued)

(52) U.S. Cl.
CPC ............ *G16H 20/13* (2018.01); *G06N 20/00* (2019.01); *G06Q 10/0833* (2013.01); *G16H 70/40* (2018.01)

(58) Field of Classification Search
None
See application file for complete search history.

(56) References Cited

U.S. PATENT DOCUMENTS 6,934,594 B2 8/2005 Loring
6,985,416 B1 * 1/2006 Lin ................. G11B 20/10527 369/47.33

(Continued)

OTHER PUBLICATIONS

Yaseen, Ahmad "Working with different SOL Server Indexes types" (Year: 2018).

(Continued)

*Primary Examiner* — Fateh M Obaid
(74) *Attorney, Agent, or Firm* — Miller Johnson

(57) ABSTRACT

A computer system for transforming a user interface according to multiple machine learning models includes a back-end timing circuit. The back-end timing circuit is configured to determine model selection parameters including an assigned pharmacy of a fill, a line of business, a time that a back-end system will receive the fill, a back-end processing channel, or a queuing priority, and select one of the machine learning models to generate a prediction of a back-end time indicating an amount of time to complete a set of back-end processes to prepare the fill for shipping. The back-end timing circuit is configured to determine a transit time corresponding to physical delivery of the fill to an address of a user. A notification circuit is configured to selectively produce a modification of the user interface based on a user promise date.

23 Claims, 13 Drawing Sheets

Related U.S. Application Data a continuation-in-part of application No. 16/731,502, filed on Dec. 31, 2019, now abandoned.

(60) Provisional application No. 62/867,832, filed on Jun. 27, 2019.

(51) Int. Cl.
*G06Q 10/0833* (2023.01)
*G16H 70/40* (2018.01)

(56) References Cited

U.S. PATENT DOCUMENTS

| | | | | |
|---|---|---|---|---|
| 7,110,841 | B1 | 9/2006 | Brearley | |
| 7,295,990 | B1 | 11/2007 | Braumoeller | |
| 7,379,781 | B2 | 5/2008 | Treichler | |
| 7,590,563 | B1 | 9/2009 | Ward | |
| 7,860,724 | B2 | 12/2010 | Chudy | |
| 7,984,809 | B1 | 7/2011 | Ramey | |
| 7,996,243 | B1 | 8/2011 | Ali | |
| 8,032,397 | B2 | 10/2011 | Lawless | |
| 8,103,377 | B1 | 1/2012 | Wong | |
| 8,265,953 | B2 | 9/2012 | Elizabeth | |
| 8,407,151 | B1 | 3/2013 | Agarwal | |
| 8,473,425 | B1 | 6/2013 | Maurer | |
| 8,560,347 | B1 | 10/2013 | Ali | |
| 8,682,474 | B2 | 3/2014 | Rotella | |
| 9,604,781 | B2 | 3/2017 | Stevens | |
| 9,916,550 | B2 | 3/2018 | Murugan | |
| 10,430,732 | B2 | 10/2019 | Zumwalt | |
| 10,484,255 | B2 | 11/2019 | Di Pietro | |
| 10,741,091 | B2 | 8/2020 | Tolman | |
| 10,796,423 | B2 | 10/2020 | Goja | |
| 10,896,048 | B1 * | 1/2021 | Markson | G16H 70/40 |
| 11,004,013 | B2 | 5/2021 | Eisenzopf | |
| 11,232,399 | B1 * | 1/2022 | Calvin | G06Q 10/087 |
| 2002/0032582 | A1 * | 3/2002 | Feeney, Jr. | G07F 17/0092 700/231 |
| 2003/0149599 | A1 | 8/2003 | Goodall | |
| 2004/0059583 | A1 | 3/2004 | O'Neill | |
| 2004/0088187 | A1 * | 5/2004 | Chudy | G16H 20/10 705/2 |
| 2004/0122713 | A1 * | 6/2004 | Hill, Sr. | G16H 20/13 705/2 |
| 2004/0225390 | A1 | 11/2004 | Keller | |
| 2005/0216111 | A1 | 9/2005 | Ooshima | |
| 2005/0228766 | A1 | 10/2005 | Roberts | |
| 2006/0277269 | A1 | 12/2006 | Dent | |
| 2007/0010904 | A1 | 1/2007 | Cheng | |
| 2007/0143169 | A1 | 6/2007 | Grant | |
| 2007/0191985 | A1 * | 8/2007 | Bain | G07F 9/002 700/232 |
| 2008/0228721 | A1 * | 9/2008 | Wahl | G06Q 10/109 |
| 2010/0088108 | A1 | 4/2010 | Machado | |
| 2010/0100396 | A1 | 4/2010 | Daven | |
| 2011/0022433 | A1 | 1/2011 | Nielsen | |
| 2011/0307265 | A1 | 12/2011 | Bannis | |
| 2012/0078673 | A1 | 3/2012 | Koke | |
| 2012/0130747 | A1 | 5/2012 | Keresman, III | |
| 2012/0173254 | A1 | 7/2012 | Korhnak | |
| 2012/0185264 | A1 | 7/2012 | Demogenes | |
| 2013/0090947 | A1 | 4/2013 | Nockley | |
| 2013/0151267 | A1 | 6/2013 | Mehdizadeh | |
| 2014/0088989 | A1 | 3/2014 | Krishnapuram | |
| 2014/0089161 | A1 | 3/2014 | Robbins | |
| 2014/0095190 | A1 | 4/2014 | Chudy | |
| 2014/0129407 | A1 | 5/2014 | White | |
| 2014/0351164 | A1 | 11/2014 | Ballenger | |
| 2015/0058034 | A1 | 2/2015 | Ayshford | |
| 2015/0154701 | A1 | 6/2015 | Jaberg | |
| 2015/0286799 | A1 * | 10/2015 | Padmani | G16H 20/10 705/3 |
| 2015/0347958 | A1 | 12/2015 | Cho | |
| 2016/0103976 | A1 | 4/2016 | Demogenes | |
| 2016/0155164 | A1 | 6/2016 | Ott | |
| 2016/0328781 | A1 | 11/2016 | Patel-Zellinger | |
| 2017/0098188 | A1 | 4/2017 | Aryeetey | |
| 2017/0193546 | A1 * | 7/2017 | Bennett | G06Q 30/0201 |
| 2018/0240539 | A1 | 8/2018 | Doherty | |
| 2019/0164636 | A1 | 5/2019 | Power | |
| 2019/0272609 | A1 | 9/2019 | Eller | |
| 2020/0039744 | A1 | 2/2020 | Lert | |
| 2020/0202993 | A1 | 6/2020 | Kaye | |
| 2020/0402627 | A1 * | 12/2020 | Rosomoff | G16H 20/10 |
| 2024/0153013 | A1 * | 5/2024 | Greenblatt | G16H 20/10 |

OTHER PUBLICATIONS

DataDirect Technologies, "Using Indexes" www.datadirect.com (Year: 2004).

Neuman, "Computer-Related Risks" Excerpts on Computer Calendar-Clock Problems Peter G. Neumann (Year: 2000).

Drkusic "All about Indexes" The Very Basics Database Iternals (Year: 2016).

Microsoft Visio 2010—Module 1, "Chapter 16, Gant Charts" (Year: 2010).

Fine et al., "Project Timelines and Gant Charts" UC Davis (Year: 2101).

Medication supply chain management through implementation of a hospital pharmacy computerized inventory program in Haiti (Year: 2015).

* cited by examiner

736
Delivery Schedule Database
700
Fill Priority Determination Device
704
Set Of Orders
Sorting Device
HVF Fill Determination Device
708
UOU Fill Determination Device
720
Manual Fill Determination Device
728
732
Update Device
716
Ordered Fill List Database
740
Forwarding Device
744
Manual Pick List Device
724
UOU Device
712
HVF Device Inputs
$x_1$
$x_2$
$x_3$
$x_n$
$w_1$
$w_2$
$w_3$
$w_n$
Σ
f
Sum
Activation Function
Output

COMPUTERIZED FULFILLMENT DEVICE WITH AUTOMATED PRIORITIZATION ENGINE

CROSS-REFERENCE TO RELATED APPLICATIONS

This application is a continuation-in-part of U.S. application Ser. No. 16/731,690 filed Dec. 31, 2019 and U.S. application Ser. No. 16/731,502 filed Dec. 31, 2019, and claims the benefit of U.S. Provisional Application No. 62/867,832 filed Jun. 27, 2019. The entire disclosures of the applications referenced above are incorporated by reference.

FIELD

The present disclosure relates to physical fulfillment systems and, more particularly, to physical fulfillment systems that transform user interfaces according to fulfillment parameters of remotely ordered drugs and package items for shipment.

BACKGROUND

Currently, entities such as pharmacy benefit managers (PBMs) offer mail order drug programs. For example, a user can order a prescription drug, to be fulfilled at a high-volume pharmacy, and have the prescription drug mailed to the user's residence. To fulfill the prescription drug order, the PBM processes the order to, among other tasks, verify insurance coverage of the user and assign the high-volume pharmacy to fulfill the order. In addition to shipping variations, the length of time to complete PBM processes may vary based on the particular order, the particular user, and the particular prescription drug, making a delivery date of the order difficult to predict accurately.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system is configured to control a set of fulfillment devices. The computer system includes a sorting device that receives a set of orders from a routing device. The sorting device, for each fill of a first order of the set of orders, assigns the fill to one of a set of fulfillment devices based on a type of prescription drug specified by the fill. The computer system includes a sequence determination device configured to receive a first set of fills assigned to a first fulfillment device of the set of fulfillment devices. The sequence determination device adds the first set of fills to a first sequence corresponding to the first fulfillment device.

The sequence determination device, for each fill of the first set of fills, determines a start time based on (i) a corresponding target date of the corresponding order and (ii) a priority of the corresponding order. The sequence determination device organizes the first sequence based on the start times of the first set of fills. The computer system includes a data store configured to store, for each device of the set of fulfillment devices, a sequence that specifies a plurality of fills. The sequence also, for each fill of the plurality of fills, specifies (i) the start time and (ii) a corresponding order. The sequence for the first fulfillment device is the first sequence. The computer system includes a forwarding device configured to forward the first sequence to the first fulfillment device.

In other features, the sequence determination device is configured to receive a second set of fills assigned to a second fulfillment device of the set of fulfillment devices, add the second set of fills to a second sequence corresponding to the second fulfillment device, and organize the second sequence based on (i) a corresponding target date of the corresponding order and (ii) a priority of the corresponding order. In other features, the forwarding device is configured to forward the second sequence to the second fulfillment device.

In other features, the sequence determination device is configured to receive a third set of fills assigned to a third fulfillment device of the set of fulfillment devices, add the third set of fills to a third sequence corresponding to the third fulfillment device, and organize the third sequence based on the corresponding target date of the corresponding order. In other features, the forwarding device is configured to forward the third sequence to the third fulfillment device.

In other features, the computer system includes an update device configured to obtain a delivery schedule for a delivery destination of the corresponding order and determine a delivery need-by-time based on the delivery schedule. The update device determines an order fulfillment time based on the first sequence, calculates a difference between the delivery need-by-time and the order fulfillment time, and, in response to the difference exceeding a predetermined threshold, update the first sequence based on the delivery need-by-time. In other features, the delivery schedule is selected based on the corresponding target date of the corresponding order. In other features, the computer system includes a delivery schedule database storing a set of delivery schedules indexed according to delivery destination.

In other features, the sorting device is configured to categorize the type of prescription drug specified by the fill as (i) a first type, (ii) a second type, or (iii) a third type. The sorting device assigns the fill to: (i) the first fulfillment device in response to the type of prescription drug being the first type, (ii) a second fulfillment device of the set of fulfillment devices in response to the type of prescription drug being the second type, and (iii) a third fulfillment device of the set of fulfillment devices in response to the type of prescription drug being the third type. In other features, the first fulfillment device is a high volume filler, the second fulfillment device is a unit of use device, and the third fulfillment device represents a manual fulfillment method.

A computer-implemented method controls a set of fulfillment devices. The method includes receiving a set of orders from a routing device and, for each fill of a first order of the set of orders, assigning the fill to one of a set of fulfillment devices based on a type of prescription drug specified by the fill. The method includes receiving a first set of fills assigned to a first fulfillment device of the set of fulfillment devices and adding the first set of fills to a first sequence corresponding to the first fulfillment device. The method includes, for each fill of the first set of fills, determining a start time based on (i) a corresponding target date of the corresponding order and (ii) a priority of the corresponding order and organizing the first sequence based on the start times of the first set of fills. The method includes storing, for each device of the set of fulfillment devices, a sequence that specifies a plurality of fills and, for each fill of the plurality of fills, specifies (i) the start time and (ii) a corresponding order, wherein the sequence for the first fulfillment device is the first sequence. The method includes forwarding the first sequence to the first fulfillment device.

In other features, the method includes receiving a second set of fills assigned to a second fulfillment device of the set of fulfillment devices, adding the second set of fills to a second sequence corresponding to the second fulfillment device, and organizing the second sequence based on (i) a corresponding target date of the corresponding order and (ii) a priority of the corresponding order. In other features, the method includes forwarding the second sequence to the second fulfillment device.

In other features, the method includes receiving a third set of fills assigned to a third fulfillment device of the set of fulfillment devices, adding the third set of fills to a third sequence corresponding to the third fulfillment device, and organizing the third sequence based on the corresponding target date of the corresponding order. In other features, the method includes forwarding the third sequence to the third fulfillment device.

In other features, the method includes obtaining a delivery schedule for a delivery destination of the corresponding order, determining a delivery need-by-time based on the delivery schedule, and determining an order fulfillment time based on the first sequence. In other features, the method includes calculating a difference between the delivery need-by-time and the order fulfillment time and, in response to the difference exceeding a predetermined threshold, updating the first sequence based on the delivery need-by-time. In other features, the delivery schedule is selected based on the corresponding target date of the corresponding order. In other features, the method includes storing a set of delivery schedules indexed according to delivery destination.

In other features, the method includes categorizing the type of prescription drug specified by the fill as (i) a first type, (ii) a second type, or (iii) a third type. In other features, the method includes assigning the fill to: (i) the first fulfillment device in response to the type of prescription drug being the first type, (ii) a second fulfillment device of the set of fulfillment devices in response to the type of prescription drug being the second type, and (iii) a third fulfillment device of the set of fulfillment devices in response to the type of prescription drug being the third type. In other features, the first fulfillment device is a high volume filler, the second fulfillment device is a unit of use device, and the third fulfillment device represents a manual fulfillment method.

A computer system for transforming a user interface associated with a first user includes a data store configured to store a first order. The first order specifies: (i) a user identifier that identifies the first user and (ii) a set of fills. Each fill of the set of fills includes fill parameters. The computer system includes a pharmacy assignment device configured to receive the first order from the data store. The pharmacy assignment device also, for each fill of the set of fills obtains fill parameters for the fill from the data store and determines an assignment of the fill to an assigned pharmacy of a set of pharmacies based on the obtained fill parameters.

The computer system includes a front-end timing device configured to, for each fill of the set of fills, determine a front-end time corresponding to the fill based on a front-end delay that indicates an amount of time to complete a set of pre-fulfillment tasks for the fill. The front-end timing device is also configured to transmit the front-end time and the pharmacy assignment to a back-end timing device and obtain, from the back-end timing device, a back-end time corresponding to the fill and a transit time. The transit time corresponds to physical delivery of the fill to an address of a user. The computer system includes a user promise date device configured to, for each fill of the set of fills, calculate a fill promise date based on (i) the corresponding back-end time and (ii) the corresponding transit time. The user promise date device is also configured to select a latest one of the fill promise dates as a user promise date. The computer system includes a notification module configured to selectively produce a modification of the user interface based on the user promise date. The user interface is generated by a web portal.

In other features, the back-end timing device is configured to, for each fill of the set of fills, receive the front-end time and the fill parameters for the fill and determine the back-end time corresponding to the fill based on the front-end time and the fill parameters. In other features, the back-end timing device calculates the transit time corresponding to the fill from the assigned pharmacy to a destination associated with the first order and transmits the back-end time for the fill and the transit time for the fill to the front-end timing device.

In other features, the back-end timing device is configured to select a latest one of the back-end times for the set of fills as an order back-end time. In other features, the front-end timing device is configured to, from the front-end times for each fill of the set of fills, select a latest one of the front-end times as an order front-end time. In other features, the front-end timing device is configured to determine a latest time the first order could be transmitted to a back-end system while maintaining the order back-end time. In other features, the front-end timing device is configured to adjust the order front-end time based on the determined latest time.

In other features, the front-end timing device is configured to adjust the order front-end time to match the determined latest time. In other features, the modification of the user interface includes displaying the user promise date on the web portal. In other features, the front-end timing device is configured to, for each fill of the set of fills, attempt to complete a set of tasks for the fill. In other features, the front-end timing device is configured to, for each task in the set of tasks, update a task status to incomplete in response to a failed attempt to complete the task. In other features, the front-end timing device is configured to, for each task in the set of tasks with the task status set to incomplete, add the task to the set of pre-fulfillment tasks for the fill.

In other features, the computer system includes a plurality of lookup tables corresponding to pre-fulfillment tasks. In other features, the front-end timing device is configured to determine the front-end delay of a first fill of the set of fills by, for each task in the set of pre-fulfillment tasks for the first fill, identifying a lookup table of the plurality of lookup tables corresponding to the task, selecting a value from the identified lookup table, and updating the front-end delay based on the selected value.

In other features, each of the plurality of lookup tables is indexed by a day of week and a time of day. In other features, the day of week is determined by a day during which the front-end timing device is determining the front-end delay. In other features, the time of day is determined by a time at which the front-end timing device is determining the front-end delay. In other features, the computer system includes a split device configured to split the first order into a set of sub-orders in response to at least one fill of the set of fills being assigned to a different pharmacy from at least one other fill of the set of fills. In other features, splitting the first order includes creating a first sub-order with the at least one fill of the set of fills and creating a second sub-order with the at least one other fill of the set of fills.

In other features, the computer system includes a router device configured to route each sub-order of the set of sub-orders to the respective assigned pharmacy. In other features, assigning a first fill of the set of fills to the assigned pharmacy is based on (i) a distance between the assigned pharmacy and a destination associated with the first order, (ii) a stock of a drug associated with the first fill at the assigned pharmacy, and (iii) whether the drug associated with the first fill is a controlled substance. In other features, the fill parameters for a first fill of the set of fills include (i) a drug identifier indicating a drug for the first fill, (ii) a prescribed strength of the drug, (iii) a prescribed quantity of the drug, and (iv) a controlled substance status of the drug.

A computer method for modifying a user interface associated with a first user. The computer method includes receiving, from a data store, a first order. The first order specifies: (i) a user identifier that identifies the first user and (ii) the set of fills. Each fill of the set of fills includes fill parameters. For each fill of the set of fills, the method includes obtaining, from the data store, fill parameters for the fill. The computer method includes determining an assignment of the fill to an assigned pharmacy of a set of pharmacies based on the obtained fill parameters and determining, with a front-end timing device, a front-end time corresponding to the fill based on a front-end delay that indicates an amount of time to complete a set of pre-fulfillment tasks for the fill.

The computer method includes transmitting the front-end time and the pharmacy assignment to a back-end timing device and obtaining, from a back-end timing device, a back-end time corresponding to the fill and a transit time. The transit time corresponds to physical delivery of the fill to an address of a user. The computer method includes calculating a fill promise date based on (i) the corresponding back-end time and (ii) the corresponding transit time, selecting a latest one of the fill promise dates as a user promise date, and selectively producing a modification of the user interface based on the user promise date. The user interface is generated by a web portal.

In other features, the computer method includes, for each fill of the set of fills, receiving the front-end time and the fill parameters for the fill and determining the back-end time corresponding to the fill based on the front-end time and the fill parameters. In other features, the computer method includes calculating the transit time corresponding to the fill from the assigned pharmacy to a destination associated with the first order and transmitting the back-end time for the fill and the transit time for the fill to the front-end timing device.

In other features, the computer method includes selecting a latest one of the back-end times for the set of fills as an order back-end time and, from the front-end times for each fill of the set of fills, selecting a latest one of the front-end times as an order front-end time. In other features, the computer method includes determining a latest time the first order could be transmitted to a back-end system while maintaining the order back-end time and adjusting the order front-end time based on the determined latest time.

In other features, the computer method includes adjusting the order front-end time to match the determined latest time. In other features, the computer method includes, for each fill of the set of fills, attempting to complete a set of tasks for the fill and, for each task in the set of tasks, updating a task status to incomplete in response to a failed attempt to complete the task. In other features, the computer method includes, for each task in the set of tasks with the task status set to incomplete, adding the task to the set of pre-fulfillment tasks for the fill.

In other features, the computer method includes determining the front-end delay of a first fill of the set of fills by, for each task in the set of pre-fulfillment tasks for the first fill, identifying a lookup table of a plurality of lookup tables corresponding to the task, selecting a value from the identified lookup table, and updating the front-end delay based on the selected value.

A computer system for transforming a user interface according to a plurality of machine learning models includes a data store configured to store an order. The order specifies a set of fills, and each fill of the set of fills includes fill parameters. The system includes a back-end timing circuit configured to, for each fill of the set of fills, receive a front-end time and the fill parameters for the fill. The front-end time is based on a front-end delay that indicates an amount of time to complete a set of pre-fulfillment tasks for the fill. The back-end timing circuit is configured to determine, based on at least one of the fill parameters and the front-end time, a set of model selection parameters including at least one of an assigned pharmacy of the fill, a line of business of the fill, a time that a back-end system will receive the fill, a back-end processing channel for the fill, and a queuing priority of the fill, select one of the plurality of machine learning models based on at least a portion of the set of model selection parameters, and supply at least a portion of the set of model selection parameters to the selected machine learning model to generate a prediction of a back-end time corresponding to the fill. The back-end time indicates an amount of time to complete a set of back-end processes to prepare the fill for shipping. The back-end timing circuit is configured to determine a transit time. The transit time corresponds to physical delivery of the fill to an address of a user. The system includes a user promise date circuit configured to, for each fill of the set of fills, calculate a fill promise date based on (i) the back-end time for the fill and (ii) the transit time for the fill, and select a latest one of the fill promise dates as a user promise date. The system includes a notification circuit configured to selectively produce a modification of the user interface based on the user promise date.

In other features, the back-end timing circuit is configured to, for each fill of the set of fills, select a transit time machine learning model from the plurality of machine learning models, and determine the transit time according to a prediction output of the selected transit time machine learning model. In other features, the back-end timing circuit is configured to obtain a queuing delay value according to at least one of a current backlog of the back-end system and a current work in progress (WIP) of the back-end system and, for each fill of the set of fills, determine a back-end completion time according to the queuing delay value and the back-end time corresponding to the fill. The back-end completion time indicates a time when the set of back-end processes will be completed.

In other features, the back-end timing circuit is configured to, for each fill of the set of fills, identify one or more transit parameters of the fill including at least one of the queuing delay value, a day of the week that the fill will be shipped, a nearest carrier sorting hub to a location of the assigned pharmacy of the fill, a delivery destination of the fill, and a weekend or holiday delivery status associated with the day that the fill will be shipped, and supply the one or more transit parameters as input to the selected transit time machine learning model to generate the prediction output. In other features, the back-end timing circuit includes a queue repository configured to store data indicative of the current backlog of the back-end system or the current work in progress (WIP) of the back-end system. The back-end timing circuit is configured to obtain the queuing delay value from the queue repository, compare the queuing delay value to a specified threshold and, for each fill in the set of fills, increase the back-end time corresponding to the fill in response to the queuing delay value exceeding the specified threshold.

In other features, the transit time machine learning model comprises a decision tree based random forest model. In other features, the back-end timing circuit is configured to, for each fill of the set of fills, access a guaranteed delivery time repository. The guaranteed delivery time repository is associated with at least one delivery carrier and stores data indicative of guaranteed delivery time values provided by the delivery carrier. The back-end timing circuit is configured to determine the transit time for the fill by looking up a guaranteed delivery time value from the guaranteed delivery time repository according to a time of shipping the fill.

In other features, the queuing priority of each fill includes a planned fill status or an on-demand fill status, and the back-end timing circuit is configured to increase the back-end time for each fill of the set of fills having the planned fill status. In other features, the system includes a front-end timing circuit configured to, for each fill of the set of fills, select a front-end machine learning model from the plurality of machine learning models, and determine the front-end time corresponding to the fill according to a prediction output of the selected front-end machine learning model.

In other features, the system includes a front-end timing circuit, the back-end timing circuit is configured to select a latest one of the back-end times for the set of fills as an order back-end time, and the front-end timing circuit is configured to, from the front-end times for each fill of the set of fills, select a latest one of the front-end times as an order front-end time, determine a latest time the order could be transmitted to a back-end system while maintaining the order back-end time, and adjust the order front-end time based on the determined latest time.

In other features, the modification of the user interface includes displaying the user promise date on at least one of a web portal and a mobile application. In other features, the system includes a front-end timing circuit and a plurality of lookup tables corresponding to pre-fulfillment tasks. The front-end timing circuit is configured to determine the front-end delay of a first fill of the set of fills by, for each task in the set of pre-fulfillment tasks for the first fill, identifying a lookup table of the plurality of lookup tables corresponding to the task, selecting a value from the identified lookup table, and updating the front-end delay based on the selected value.

In other features, the system includes a split circuit configured to split the order into a set of sub-orders in response to at least one fill of the set of fills being assigned to a different pharmacy from at least one other fill of the set of fills, and a router circuit configured to route each sub-order of the set of sub-orders to the respective pharmacy assignment. In other features, the assigned pharmacy of a first fill of the set of fills is based on (i) a distance between the assigned pharmacy and a destination associated with the order, (ii) a stock of a drug associated with the first fill at the assigned pharmacy, and (iii) whether the drug associated with the first fill is a controlled substance, and the fill parameters for the first fill of the set of fills include (i) a drug identifier indicating a drug for the first fill, (ii) a prescribed strength of the drug, (iii) a prescribed quantity of the drug, and (iv) a controlled substance status of the drug.

In other features, the system includes a pharmacy assignment circuit configured to receive the order from the data store and, for each fill of the set of fills, determine the assigned pharmacy for the fill according to the fill parameters of the fill, and a front-end timing circuit configured to, for each fill of the set of fills, determine the front-end time corresponding to the fill. In other features, the time is a calendar date, and the fill parameters include a day of the week that the back-end system will receive the fill.

A computer system for transforming a user interface according to a plurality of machine learning models includes memory hardware configured to store computer-executable instructions and an order. The order specifies a set of fills, and each fill of the set of fills includes fill parameters. The system includes processor hardware configured to execute the instructions. The instructions include, for each fill of the set of fills, receiving a front-end time and the fill parameters for the fill. The front-end time is based on a front-end delay that indicates an amount of time to complete a set of pre-fulfillment tasks for the fill. The instructions include determining, based on at least one of the fill parameters and the front-end time, a set of model selection parameters including at least one of an assigned pharmacy of the fill, a line of business of the fill, a time that a back-end system will receive the fill, a back-end processing channel for the fill, and a queuing priority of the fill, selecting one of the plurality of machine learning models based on at least a portion of the set of model selection parameters, and supplying at least a portion of the set of model selection parameters to the selected machine learning model to generate a prediction of a back-end time corresponding to the fill. The back-end time indicates an amount of time to complete a set of back-end processes to prepare the fill for shipping. The instructions include determining a transit time. The transit time corresponds to physical delivery of the fill to an address of a user. The instructions include calculating a fill promise date based on (i) the back-end time for the fill and (ii) the transit time for the fill, selecting a latest one of the fill promise dates as a user promise date, and selectively producing a modification of the user interface based on the user promise date.

A computerized method of transforming a user interface according to a plurality of machine learning models includes, for each fill of a set of fills specified by an order. Each fill of the set of fills includes fill parameters. The method includes receiving a front-end time and the fill parameters for the fill. The front-end time is based on a front-end delay that indicates an amount of time to complete a set of pre-fulfillment tasks for the fill. The method includes determining, based on at least one of the fill parameters and the front-end time, a set of model selection parameters including at least one of an assigned pharmacy of the fill, a line of business of the fill, a time that a back-end system will receive the fill, a back-end processing channel for the fill, and a queuing priority of the fill, selecting one of the plurality of machine learning models based on at least a portion of the set of model selection parameters, and supplying at least a portion of the set of model selection parameters to the selected machine learning model to generate a prediction of a back-end time corresponding to the fill. The back-end time indicates an amount of time to complete a set of back-end processes to prepare the fill for shipping. The method includes determining a transit time. The transit time corresponds to physical delivery of the fill to an address of a user. The method incudes calculating a fill promise date based on (i) the back-end time for the fill and (ii) the transit time for the fill, selecting a latest one of the fill promise dates as a user promise date, and selectively producing a modification of the user interface based on the user promise date.

In other features, the method includes, for each fill of the set of fills, selecting a transit time machine learning model from the plurality of machine learning models, and determining the transit time according to a prediction output of the selected transit time machine learning model. In other features, the method includes obtaining a queuing delay value according to at least one of a current backlog of the back-end system and a current work in progress (WIP) of the back-end system and, for each fill of the set of fills, determining a back-end completion time according to the queuing delay value and the back-end time corresponding to the fill. The back-end completion time indicates a time when the set of back-end processes will be completed.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
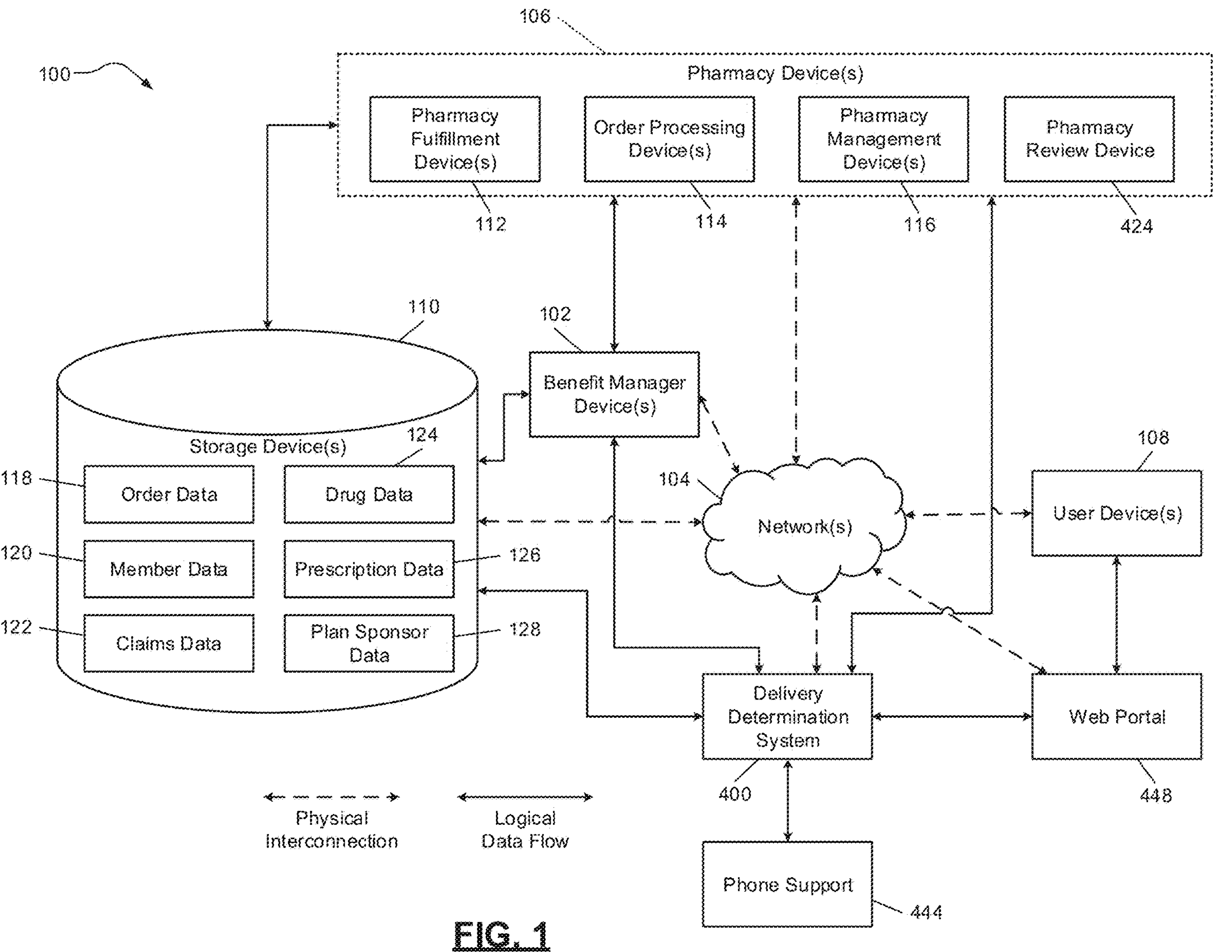
FIG. 1 is a functional block diagram of an example system including a high-volume pharmacy.

Notifying a user of a user promise date (UPD)—that is, an expected delivery date, also known as a target date—of a prescription (RX) drug order allows the user to plan for arrival of RX drugs. The UPD may be uploaded to a website of a pharmacy benefits manager (PBM) for display in a personalized page of the user. That way, after the UPD has been calculated, a user interface of the user's personalized page is modified to reflect the UPD. The user can be readily informed of the updated information without needing to contact the PBM or a pharmacy to determine when to expect their RX drug order. This increased transparency may improve the relationship between the PBM or pharmacy and the user.

In various implementations, the UPD is calculated based on time periods estimated (based on historical data, for example) for front-end processes and back-end processes. Processing and fulfillment of an RX order may be split between a so-called "front end" and a so-called "back end," respectively. However, this bifurcation is a matter of nomenclature and not a requirement of the disclosure. For example, some processes or elements described as "front-end" could instead be categorized as "back-end" and vice versa. In the case of a mail order RX drug, the UPD further incorporates an estimated transit time from a fulfilling pharmacy to a residence of the user or other destination associated with the user. The RX drug order may be assigned to the fulfilling pharmacy by front-end processes.

When an order is first received from, for example, a prescribing physician, the order may be automatically assigned to a pharmacy based on RX drug stock at the pharmacy, proximity of the pharmacy to the order destination, user preference, etc. Once assigned, the order is adjudicated and a set of remaining tasks is determined. Adjudication may include, as an example, determining prescription coverage under the user's prescription plan. The remaining tasks may include, as an example, pharmacy review—the pharmacist may review the user's health history to determine whether there are any contraindications to the prescribed drug. In various implementations, if the order is a refill that is identical to a previous order, there may be no remaining tasks for the order post-adjudication. However, if the order is a new order, there may be a non-empty set of remaining tasks post-adjudication.

A front-end timing device receives the remaining task set and, in various implementations, identifies a corresponding lookup table based on which tasks are present in the task set. From the lookup table, the front-end timing device obtains an estimated front-end delay corresponding to each remaining task category. For example, the estimated front-end delays included in the lookup tables may be based on machine learning models that predict delay times for each task. In various implementations, the lookup table can include concurrent or consecutive indicators that identify which tasks can be completed concurrently with other tasks and which tasks need to be completed consecutively.

Based on the estimated front-end delays, the front-end timing device calculates a front-end need-by time (which can also be referred to as a front-end completion time or as a front-end estimate) indicating when the front end is expected to have completed the remaining tasks associated with the order and be ready to transmit the order to the back end. In various implementations, a machine learning model may be used to generate a prediction for the front-end need-by time. In various implementations, the type of prescription (as one example rubric, the types may be new prescription, first renewal prescription, and subsequent renewal prescription) may be used as an input to the machine learning model. In other implementations, separate machine learning models may be defined and trained for various types of prescriptions, various pharmacies, various days of the week, various lines of business, various processing channels, and so on. Parameters or protocols associated with an order may then be used to select which model to use to make a prediction for the order.

Once the front-end timing device determines the estimated front-end delay, the front-end timing device transmits the estimated front-end delay along with fill parameters to a back-end timing device to obtain an estimated back-end delay and an estimated transit delay. The back-end timing device predicts a back-end need-by time (which can also be referred to as a back-end completion time or as a back-end estimate) indicating when the back-end processes will be completed and the order will be physically released for delivery to the user—for example, when the order can be physically placed on a shipping carrier's vehicle for transportation to the user's residence.

The transit time may include the time between the back-end need-by time (which may describe when the order is packaged and present at a shipping hand-off point, such as a loading dock) and the time that the order leaves the pharmacy. In various implementations, a combined time encompassing both the back-end need-by time and the transit time is determined, as described in more detail below.

In various implementations, the front-end need-by time may indicate a specific date and time at which fulfillment can begin, the back-end need-by time may indicate a specific date and time at which shipping can occur, and the transit time may indicate a specific date and time at which the order will arrive at the destination. In such cases, the combined time may be the specific date and time at which the order will arrive at the destination. In other implementations, the back-end need-by time may describe a delay between fulfillment beginning and shipment beginning. This delay may be expressed as a number of hours or a number of business hours (including only those hours during which the pharmacy is open), and is not limited to integer values. Similarly, the transit time may be expressed as a number of hours or a number of business hours, where business hours reference the operating hours of the shipping company.

Based on the front-end need-by time, the back-end need-by time, and the transit time, a UPD device can calculate the UPD, which represents a date the user can expect to receive their RX drug order. Once the UPD is calculated, the UPD may be transmitted to the user by, for example, sending the user a text message or an email. Additionally, on a web portal that a user accesses for managing their RXs, a user interface of the user's personalized page may be transformed based on the UPD. For example, the UPD may be uploaded, delivery dates may be displayed in calendar form, an interactive map may be updated according to a stage in the delivery process the order has reached, etc.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
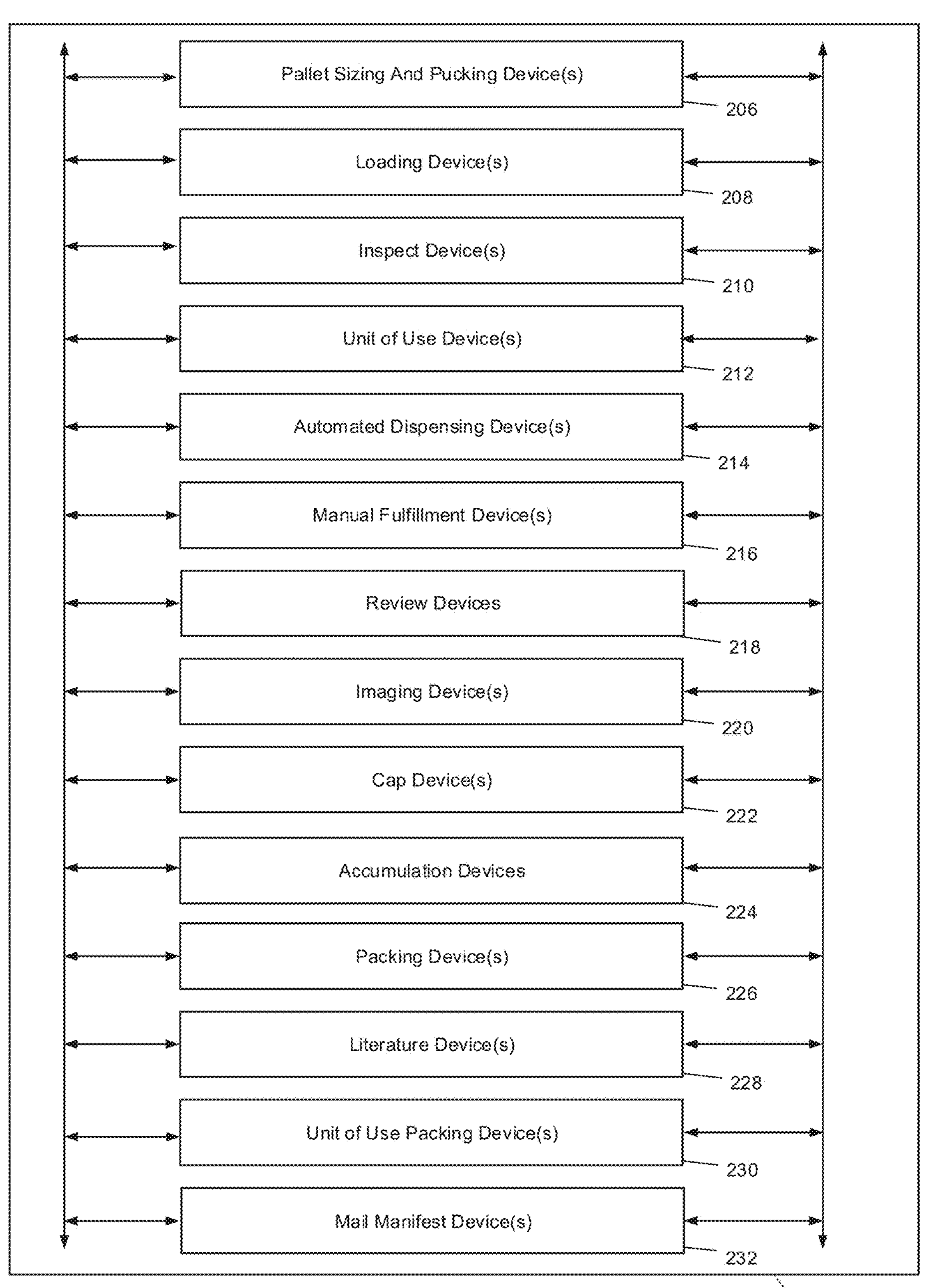
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device (s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
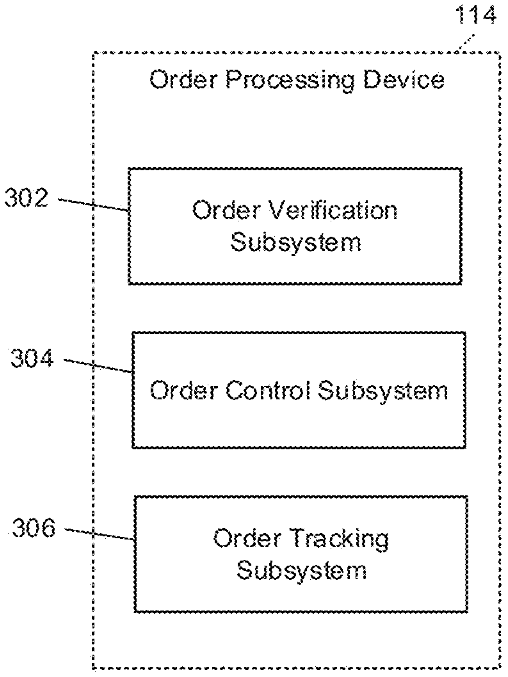
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver a pallet from the loading device 208 to the manual fulfillment device 216, to deliver a pallet from the loading device 208 to the automated dispensing device 214, and, to deliver paperwork from the literature device 228 to the packing device 226.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

User Promise Date Determination Control

Figure 4:
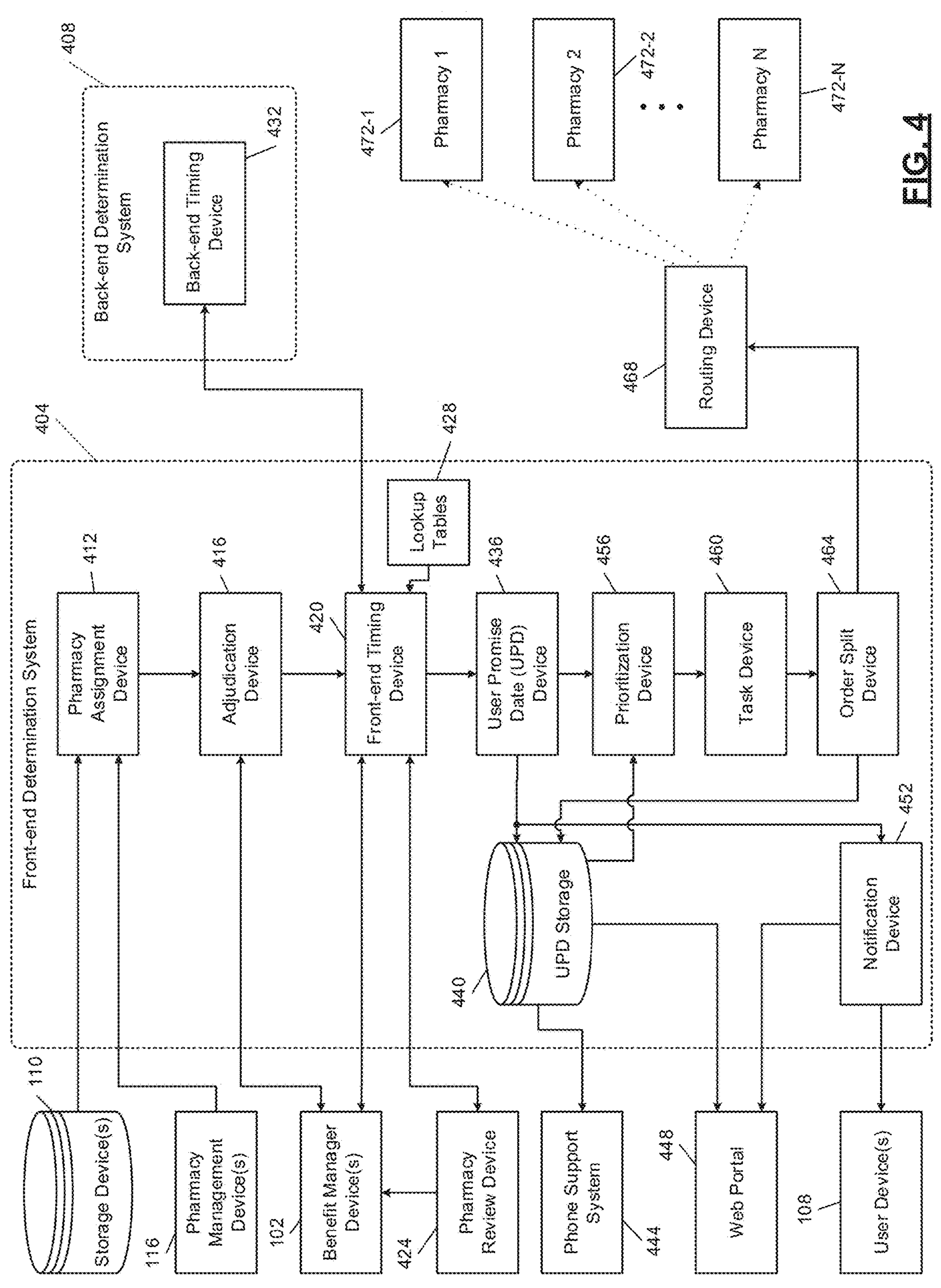
FIG. 4 is a functional block diagram of an example user promise date determination system.

FIG. 4 illustrates a functional block diagram of an example implementation of a delivery determination system 400. The delivery determination system 400 includes a front-end determination system 404 and a back-end determination system 408. In this example, multiple processes are performed in the front-end determination system 404 including pharmacy assignment, adjudication, order splitting, and order routing.

When an order is placed, such as when a prescription (RX) drug order is received for a user, the order is stored in the storage device 110. In various implementations, the storage device 110 may receive orders from a prescribing physician using the network 104 or the benefit manager device 102 may receive the order and store the order in the storage device 110. In various implementations, the order may be a non-prescription drug order, such as for an over-the-counter (OTC) medication.

In various implementations, the front-end determination system 404 includes a pharmacy assignment device 412. The pharmacy assignment device 412 retrieves orders from the storage device 110 and identifies a set of pharmacies from the pharmacy management device 116. The pharmacy management device 116 stores, for each pharmacy, a location of the pharmacy, RX drug stock, a cost to fill for each RX drug, and whether controlled RX drugs (that is, drugs listed on a schedule, such as under the Controlled Substance Act) are stocked at the pharmacy.

After the pharmacy assignment device 412 retrieves the order from the storage device 110, the pharmacy assignment device 412 parses the order to identify each fill included in the order. Each order may include one or more fills, each fill corresponding to a different RX drug or a different dosage of an RX drug. Each fill has corresponding fill parameters such as (i) a drug identifier, (ii) a dosage, (iii) an amount, (iv) a user identity, (v) a prescribing physician, etc. The pharmacy assignment device 412 assigns a pharmacy to each fill of the order. The pharmacy assignment may be based on (i) the proximity of the pharmacy to a destination, such as a user's residence associated with the order, (ii) an RX drug stock at each pharmacy for the RX drug of the corresponding fill, (iii) a cost to fill the RX drug of the corresponding fill, and/or (iv) pharmacy compatibility—for example, a health plan for the military may dictate the use of plan-exclusive pharmacies—and/or (v) a type of RX drug—for example, controlled or non-controlled.

After the pharmacy assignment device 412 assigns a pharmacy to each fill, the order proceeds to an adjudication device 416. The adjudication device 416 may adjudicate a claim associated with the order using insurance information of the user. In various implementations, the adjudication device 416 transmits the order to the benefit manager device 102 to perform adjudication, as discussed above with respect to FIG. 1. After adjudication is performed, the adjudication device 416 determines whether the claim associated with the order is approved or rejected. In either instance, a front-end timing device 420 receives the order and calculates a front-end need-by time.

In various implementations, the front-end timing device 420 identifies remaining tasks of the order to calculate a front-end need-by time. The remaining tasks represent items that need to be completed before the order can be transmitted to the back-end. For example, if the adjudication is approved, there may be no tasks remaining for the front-end determination system 404 to complete. In such a scenario, the front-end need-by time of the order is when adjudication was completed.

In various implementations, a fill may require additional levels of review, which result in one or more remaining tasks. For example, if the fill is classified as new, the front-end timing device 420 may transmit the fill to a pharmacy review device 424 for detailed pharmacist review and approval.

When the fill is similar to a previous fill with at least one fill parameter of the fill being different, the front-end timing device 420 classifies the fill as needing less in-depth pharmacist review. For each level of pharmacist review, a lookup table 428 includes a corresponding expected delay. In various implementations, the lookup table 428 is indexed according to the present day of the week and the present time. For example, if the fill is being transmitted to the pharmacy review device 424 at 5 pm on a Friday, pharmacy staffing information may indicate that a pharmacist will not be available at the corresponding pharmacy until Monday at 9 am. Moreover, Monday at 9 am may, on average, be a day and time when the list of orders for the pharmacist to review is the longest. Therefore, the estimated delay is based on the level of necessary pharmacist review as well as the day of the week and time the fill will be transmitted to the pharmacy review device 424. In instances where the fill is identical to a previous fill, pharmacist review may be unnecessary and the corresponding delay for this task may therefore be zero.

The lookup tables 428 include a lookup table for each remaining task. Each lookup table may be indexed by the day of the week and the time. Once an estimated delay is determined for each remaining task, the front-end timing device 420 calculates the front-end need-by time for each fill of the order and transmits the order and the front-end need-by time to a back-end timing device 432 included in the back-end determination system 408. In various implementations, the estimated delay for each remaining task of a fill is summed. Since certain tasks may be performed concurrently, the task incurring the longest delay is selected from the concurrently performed tasks and summed with remaining consecutive tasks.

The back-end timing device 432 determines a back-end need-by time and a transit time for each fill of the order. The back-end need-by time indicates when a pharmacy assigned by the routing device 468 will have completed all back-end processes and the order can be shipped. The transit time represents an estimated delivery time from the assigned pharmacy to a destination associated with the order, such as a user's residence. The back-end need-by time and the transit time are transmitted to the front-end timing device 420. A user promise date (UPD) device 436 obtains the front-end need-by time, the back-end need-by time, and the transit time and calculates a UPD for each fill of the order based on the three values. In various implementations, a combined time may be used instead of separate back-end need-by and transit times.

The UPD is transmitted to UPD storage 440 for distribution to a phone support system 444 and a web portal 448. The UPD is also transmitted to a notification device 452. In various implementations, the notification device 452 can update interfaces generated by the web portal 448 based on the UPD. For example, the web portal 448 may generate a user interface for each user that logs on to the web portal 448. When the UPD for a particular user has been calculated, the notification device 452 may output a signal that transforms the user interface of the web portal 448 for the user. In one example, if the UPD is within three days of the current date, the user interface of the web portal 448 may be transformed so as to direct the user's attention to the UPD at logon time. Alternatively, if the UPD is over a week away from the present date, the UPD may not be visually emphasized at logon time.

Additionally, when the user logs on to the web portal 448, the web portal 448 may access the UPD storage 440 to identify any UPDs that are associated with the user and may list the associated UPDs on a particular screen of the web portal 448. The phone support system 444 may access the UPD storage 440 to provide the user with any associated UPDs during a phone call. In various implementations, the notification device 452 may generate and transmit an alert to the user device 108 in response to the UPD device 436 calculating the UPD. The alert indicates that the UPD is available and may include the UPD itself.

After the UPD is calculated, a prioritization device 456 receives the UPD of each fill and prioritizes each fill based on the UPD of each fill. In various implementations, each fill in the UPD storage 440 may be prioritized based on the front-end need-by time to ensure the back-end determination system 408 receives the order by the front-end need-by time. Additionally, the prioritization device 456 may adjust the front-end need-by time for certain fills. For instance, if the front-end need-by time can be adjusted to a later time or date and the fill will still be delivered by the UPD, the front-end need-by time may be adjusted to the latest possible front-end need-by time that maintains the UPD. If the prioritization device 456 adjusts the front-end need-by time, then the prioritization device 456 can adjust the priority order of the fill based on the adjusted front-end need-by time so that fills with earlier front-end need-by times can be processed earlier.

Once prioritized, the order continues to a task device 460, where the remaining tasks identified by the front-end timing device 420 are completed. After the order is transmitted to the task device 460, the front-end determination system 404 processes and completes the remaining tasks, and, once all tasks are completed, the order continues to an order split device 464. The order split device 464 determines which pharmacy is assigned to each fill of the order. If fills of the order are assigned to multiple pharmacies—that is, at least one fill is assigned to a pharmacy that is different from an assigned pharmacy of another fill within the order—then the order is split into sub-orders based on the assigned pharmacy of the fill.

In various implementations, one fill of an order may be a controlled RX drug that only particular pharmacies can fill. If all other fills included in the order can be filled by a pharmacy that is closer and cheaper than a controlled RX drug pharmacy, the pharmacy assignment device 412 may assign fills in the same order to different pharmacies. Then, the order split device 464 will split the order into a first sub-order including the controlled RX drug fill(s) and a second sub-order including the non-controlled RX drug fills.

Once the order split device 464 splits the order based on the assigned pharmacies of each fill, the order and/or each sub-order is transmitted to the routing device 468. The routing device 468 transmits each order (or, if split, each sub-order) to the assigned pharmacy. Pharmacy 1 472-1, pharmacy 2 472-2, and pharmacy N 472-N are shown in FIG. 4 as examples, where N is a positive integer. In various implementations, each fill of the order may be assigned to the same pharmacy, resulting in the order split device 464 keeping the order together and the routing device 468 routing the order to a single pharmacy, such as pharmacy 2 472-2.

User Promise Date Flowcharts

Figure 5A:
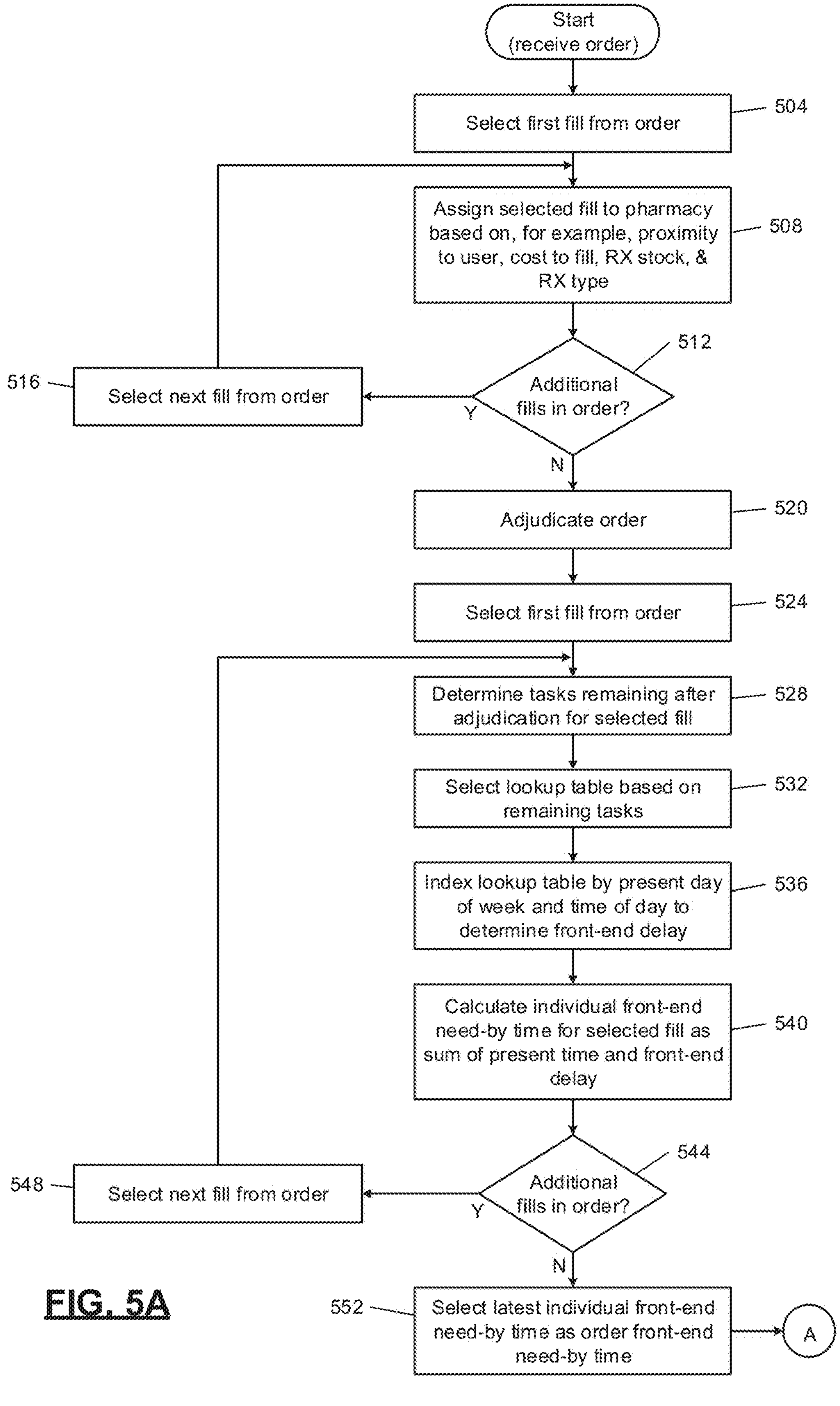
FIG. 5A is a flowchart of example determination of a front-end need-by time of an order.
Figure 5B:
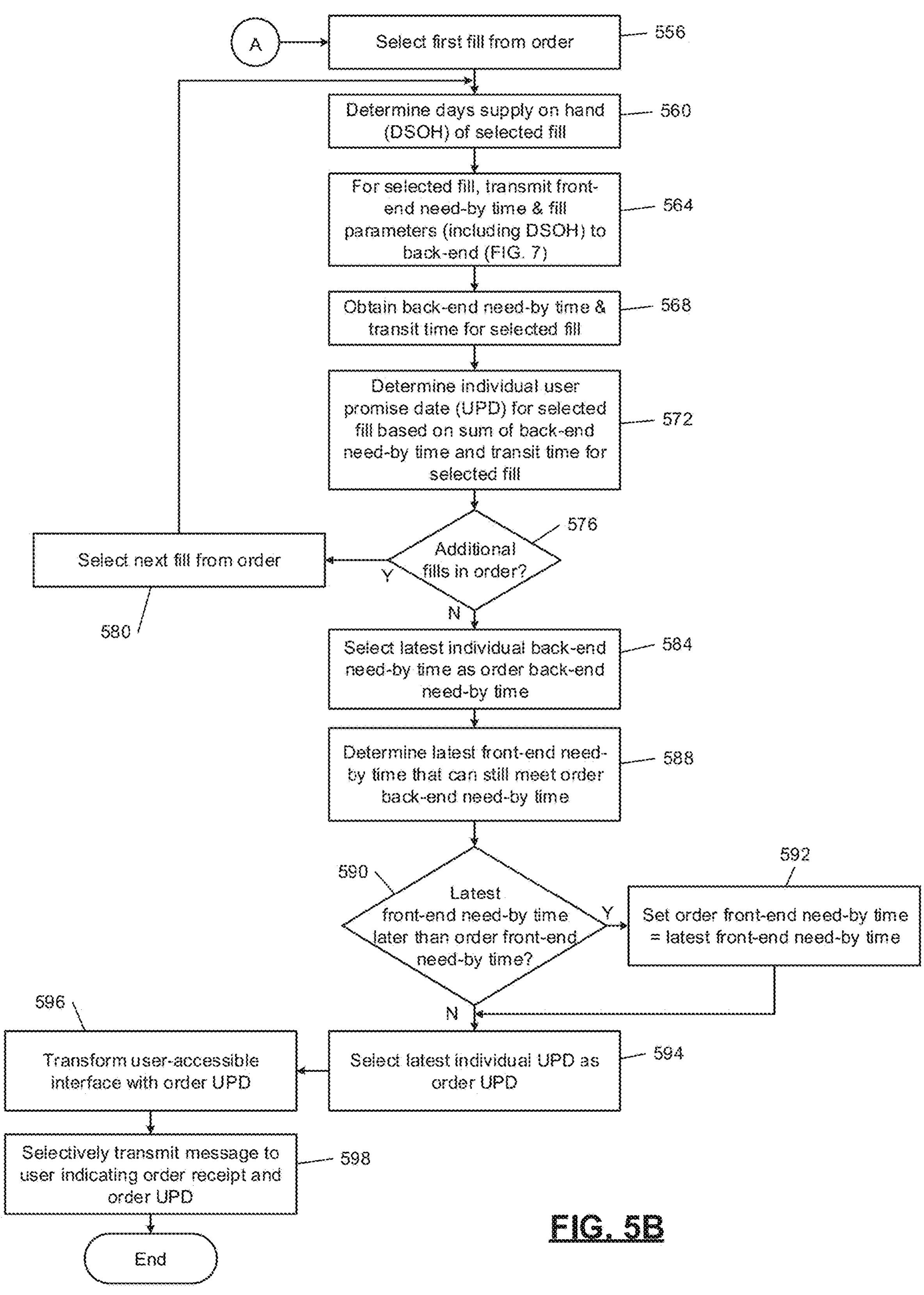
FIG. 5B is a flowchart of example determination of a user promise date of an order.

FIGS. 5A and 5B together form a flowchart showing example operations related to user promise data determination and user interface transformation. FIG. 5A illustrates example determination of front-end need-by time for an order. Control begins at 504 when an order is received. Control selects a first fill from the order. As described above, each order may include multiple fills and each fill corresponds to an RX drug.

After the first fill is selected, control continues to 508 to assign the selected fill to a pharmacy based on, for example, a proximity of the pharmacy to the user's residence (or other destination associated with the selected fill), a cost to fill the selected fill, an RX drug stock, and an RX drug type. The pharmacy may be selected from a set of pharmacies and each pharmacy included in the set may be classified based on the RX drug type the pharmacy can fulfill. For example, as described above, multiple RX drugs are classified as controlled drugs while other drugs are classified as non-controlled drugs. Therefore, the RX drug type may distinguish between controlled and non-controlled drugs, meaning that one of the pharmacy assignment factors is whether a pharmacy fills controlled drugs.

After a pharmacy is assigned to the selected fill at 508, control continues to 512 to determine whether the order includes additional fills. If yes, control proceeds to 516 to select the next fill of the order and returns to 508. Otherwise, control continues to 520 where the order is adjudicated. As described above, during adjudication of an order, the order is either approved or rejected. In either scenario, the order may require additional tasks to be performed for the order for certain fills included in the order to be ready for fulfillment. Therefore, control identifies any remaining tasks associated with fills of the order.

After adjudication at 520, control proceeds to 524 to select the first fill from the order. At 528, control determines whether tasks are remaining for the selected fill after adjudication. Control proceeds to 532, where, for each remaining task, a lookup table is selected based on the remaining tasks. The selected lookup table for a remaining task includes estimated delays that correspond to the remaining task. Additionally, each lookup table is indexed by a present day of the week and a present time of day. At 536, control indexes the lookup table corresponding to each remaining task of the selected fill to determine the estimated front-end delay associated with the task for the present day of the week and the present time of day. Control continues to 540 to calculate an individual front-end need-by time that is specific to the selected fill. In various implementations, the individual front-end need-by time of the selected fill is a sum of the present time and the determined front-end delay of each remaining task. In various implementations, a lookup table may encompass all potential remaining tasks corresponding to the selected fill, resulting in a single lookup table being referenced for each selected fill to determine the front-end delay.

Once the individual front-end need-by time is determined for the selected fill, control continues to 544 to determine if the order includes additional fills. If yes, control proceeds to 548, where the next fill of the order is selected, and then returns to 528 to determine the remaining tasks associated with the next fill. Otherwise, control continues to 552 where control selects the latest individual front-end need-by time from all the individual front-end need-by times of the fills in the order as an order front-end need-by time. Control then continues to 556 in FIG. 5B.

At 556 of FIG. 5B, control selects the first fill of the order. At 560, control determines a days supply on hand (DSOH) of the selected fill. The DSOH of the selected fill indicates a remaining number of days of medication the user may still possess from a previously filled RX. The DSOH may be estimated based on when the user received the previously filled RX and on the RX regimen, assuming 100% adherence to the RX regimen. In various implementations, the determined DSOH may influence the prioritization of a selected fill during front-end processing and/or back-end processing, with a lower DSOH leading to a higher priority.

Control continues to 564, where control transmits the individual front-end need-by time of the selected fill as well as the fill parameters of the selected fill to a back-end system. Then, at 568, control obtains a back-end need-by time and a transit time for the selected fill from the back-end system. Control continues to 572 to determine an individual UPD for the selected fill. In various implementations, the individual UPD for the selected fill is a sum of the back-end need-by time and the transit time for the selected fill. Control proceeds to 576 to determine if the order includes additional fills. If yes, control continues to 580 to select the next fill in the order and returns to 560 to process the next fill. Otherwise, control continues to 584. At 584, control selects the latest individual back-end need-by time from all the individual back-end need-by times of the order as an order back-end need-by time.

At 588, control determines a latest front-end need-by time of the order at which the order back-end need-by time can still be met. That is, control calculates a latest possible time that the front-end processes of the order can be completed for the order to maintain the order back-end need-by time. Control continues to 590 where control compares the determined latest front-end need-by time to the order front-end need-by time. If the latest front-end need-by time is later than the order front-end need-by time, control proceeds to 592 to set the order front-end need-by time equal to the latest front-end need-by time. Otherwise, control continues to 594. At 594, control selects the latest of the individual UPDs as the order UPD.

Control continues to 596 where control transforms a user-accessible interface based on the order UPD. For example, as described above, a personalized page associated with the user is accessible using a web portal. The personalized page may be transformed based on the order UPD. Control then proceeds to 598 to selectively transmit a message to the user that indicates the order was received that includes the order UPD. For example, in various implementations, a text or an email may be sent to the user once the UPD has been calculated. Then, control ends.

Figure 6:
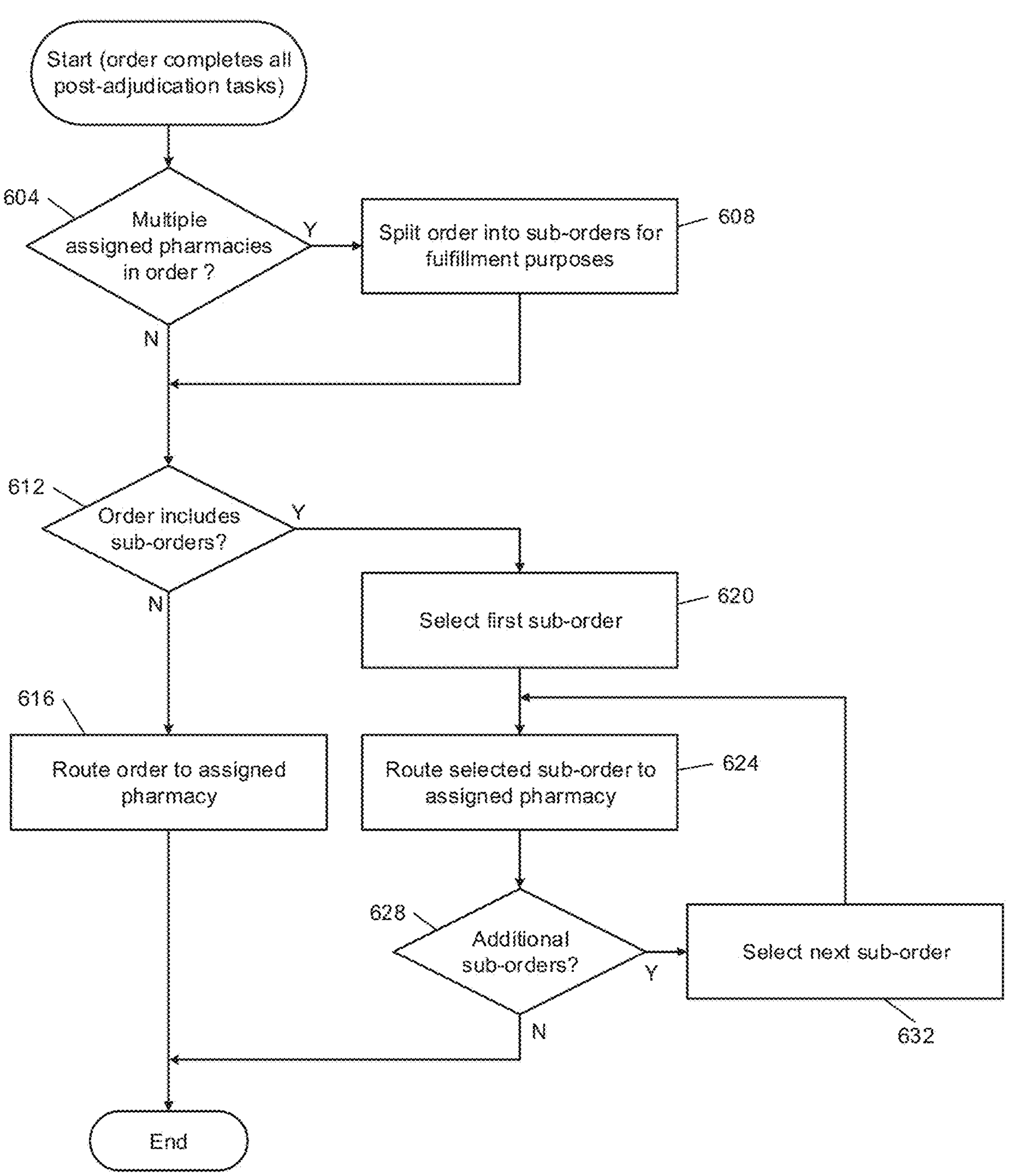
FIG. 6 is a flowchart of example dispatch of orders to assigned pharmacies.

FIG. 6 illustrates a flowchart of an example order being dispatched. Control begins after the order has completed all of the post-adjudication tasks discussed above. Once all tasks have been completed, control proceeds to 604 to identify whether the order includes multiple assigned pharmacies. That is, control determines whether at least one fill included in the order is assigned to a pharmacy different from at least one other fill included in the order. If yes, control proceeds to 608 to split the order into sub-orders based on the pharmacy assignment for fulfillment purposes. Otherwise, control proceeds directly to 612.

At 612, control determines if the order includes sub-orders. If no, control continues to 616 to route the order to the assigned pharmacy and then control ends. Otherwise, control proceeds to 620 to select the first sub-order of the order. At 624, control routes the selected sub-order to the assigned pharmacy. Control proceeds to 628 to determine if the order includes additional sub-orders. If yes, control continues to 632 to select the next sub-order and returns to 624 to route the next sub-order. Otherwise, control ends.

Priority Control and Flowcharts

Figure 7:
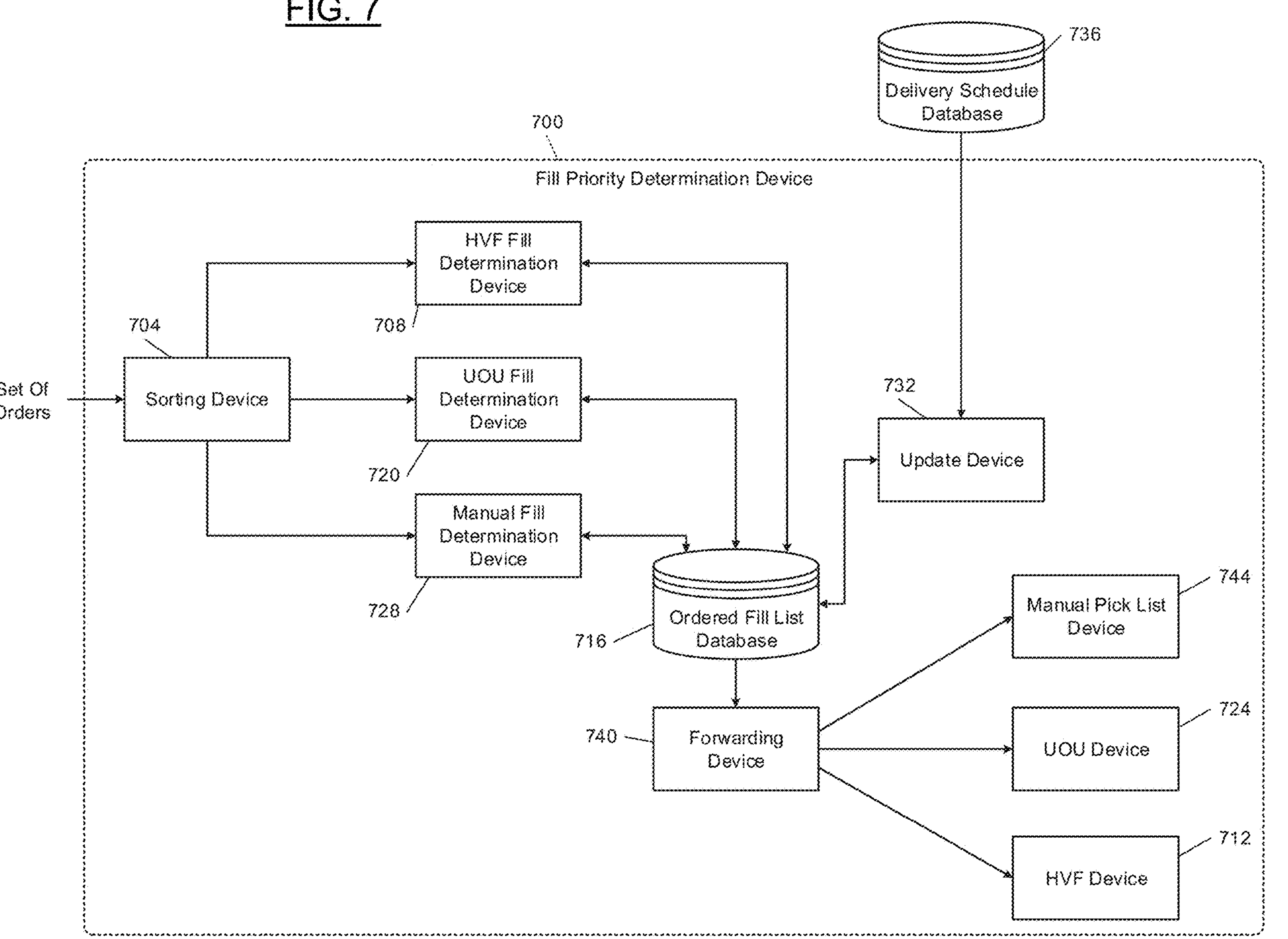
FIG. 7 is a functional block diagram of an example fill priority determination system of orders routed to a pharmacy.

FIG. 7 illustrates a functional block diagram of an example fill priority determination device of orders routed to a pharmacy. For example, the fill priority determination device 700 shown may be located at one of the pharmacies of FIG. 4. The fill priority determination device 700 receives a set of orders routed to the pharmacy by, for example, the routing device 468 of FIG. 4. The set of orders may be routed to or obtained by the corresponding pharmacies at predetermined intervals, for example, once per day, or once the front-end determination system 404 of FIG. 4 completes front-end processing.

The fill priority determination device 700 includes a sorting device 704 that receives the set of orders routed to the associated pharmacy. The sorting device 704 may obtain the set of orders at predetermined intervals, for example, at the beginning of each day, in order to update an organization or placement of fills of each order based on order priority and the corresponding UPD of the order. The order priority, for example, may include the DSOH or an indication of a higher priority based on a user request for expedited shipping. Similarly, the order priority may be lower based on the DSOH. The sorting device 704 organizes the fills of incoming orders according to a device type performing the fill. The device type that performs the fill may depend on a type of RX drug. The device types include: (i) a high volume filler (HVF), (ii) a unit of use (UOU) device (such as 212 of FIG. 2), and (iii) a manual fulfillment list.

The sorting device 704 generates and adds a list for each device type for an incoming order. A HVF type list includes fills of the incoming order that will be performed by the HVF. Similarly, the UOU type list includes fills of the incoming order that will be performed by the UOU device, and the manual type list includes fills that will be filled manually for the incoming order. In various implementations, the sorting device 704 generates a fill list for each device type for each order of the set of orders. The sorting device 704 may sort fills according using any suitable sorting technique, such as a selection sort, a bubble sort, an insertion sort, a merge sort, a recursive sort, or a quick sort. Then, an HVF fill determination device 708 generates an HVF list that maintains a particular placement (arrangement) of each fill in the HVF list for each order indicating a route of fulfillment. The HVF fill determination device 708 receives the HVF list indicating the fills of the order filled by an HVF device 712.

The HVF fill determination device 708 determines a location within the high volume pharmacy of each fill in the HVF list. The location of each fill indicates which tower in the high volume pharmacy distributes the RX drug of the corresponding fill. Each tower is a group of RX drug counting canisters. Based on the location of each fill in the HVF list, the HVF fill determination device 708 determines a route of the HVF device 712 and organizing of the fills within the HVF list. In various implementations, the route is determined based on an overall distance travelled, preferring a shorter overall distance travelled.

In other implementations, a route start location is determined based on which tower of the identified locations has a fewest number of pallets in progress. That is, the HVF fill determination device 708 selects the route start location based on which tower has the shortest wait time to be filled. Then, the HVF fill determination device 708 determines, from the route start location, the remaining route based on the number of pallets in progress in each tower. Alternatively, the remaining route may be determined based on the overall distance travelled from the route start location or a combination of the pallets in progress in each tower and the overall distance travelled.

Once the route is determined, the HVF fill determination device 708 obtains routes of previously processed fills of other orders stored in an ordered fill list database 716. The ordered fill list database 716 maintains, for each device type, an ordered fill list indicating a priority (based on placement within the list) for fulfillment of the set of orders. For example, the HVF ordered fill list includes, for each order, an HVF list ordered based on the determined route. The ordered fill lists are updated and sorted according to an order start time. The order start time for each list is based on the order UPD and the order priority. To avoid confusion between the term order referring to a prescription order and the term order referring to a specific sequence of items from first to last, an ordered fill list could also be called a fill list sequence or a sequence of fill lists.

Therefore, after the HVF fill determination device 708 obtains the corresponding HVF ordered fill list, the HVF fill determination device 708 determines a placement of the present order within the HVF ordered fill list according to the order start time and adds the present order to the HVF ordered fill list. In various implementations, to increase efficiency, the order start time of the present order may be adjusted based on similar routes of orders in the HVF ordered fill list. That is, if the present order is assigned a similar or identical route to another order in the HVF ordered fill list, then the present order may be assigned the same start time and to the same pallet.

A UOU fill determination device 720 receives the UOU list including fills of the order that are filled by a UOU device 724. The UOU fill determination device 720 determines an order start time for each order in the UOU list based on the order priority and the order UPD. In various implementations, the order start time is based on an average amount of time to complete the fulfillment of the UOU list. Then, the UOU fill determination device 720 adds the UOU list of the present order to a corresponding UOU ordered fill list stored in the ordered fill list database 716 based on the order start time and the order start times of the UOU lists presently in the UOU ordered fill list.

A manual fill determination device 728 receives the manual list from the sorting device 704. The manual fill determination device 728 determines an order start time for each manual list based on the order UPD and/or order priority. The manual list is then added to a manual ordered fill list stored in the ordered fill list database 716 based on the order start time. In various implementations, the placement within each of the ordered fill lists may be determined based on a fill end time, indicating when the fill is to be completed.

An update device 732 obtains the HFV, UOU, and manual ordered fill lists from the ordered fill list database 716 and a delivery schedule from a delivery schedule database 736. The update device 732 is configured to adjust or update placement or order start time of orders in the ordered fill lists based on the schedule of the delivery truck that delivers the corresponding order to the delivery destination. For example, if the order start time of one of the orders in the HVF ordered fill list would result in the corresponding order arriving at the corresponding delivery truck less than a predetermined time prior to departure, for example, using a one hour buffer time, the update device 732 updates the placement of the order in the HVF ordered fill list. The update ensures that the corresponding order arrives at the corresponding delivery truck prior to the predetermined time. For example, the update device 732 may update the placement of the order in the HVF ordered fill list by modifying a file that stores the HVF ordered fill list to change an order of entries in the file.

In various implementations, the update device 732 updates the HVF, UOU, and manual ordered fill lists after the set of orders is processed and included in the ordered fill list database 716. Alternatively, the update device 732 may update the ordered fill list database 716 as fills are added to each of the ordered fill lists. In various implementations, the update device 732 updates the order start time instead of the organization of the ordered fill lists.

After the update device 732 completes the updating of the ordered fill lists, a forwarding device 740 forwards the HVF ordered fill list to the HVF device 712, the UOU ordered fill list to the UOU device 724, and the manual ordered fill list to a manual pick list device 744. For example, the forwarding device may forward a list by transmitting the list over a communication interface. The manual pick list device 744 may be a mobile computing device configured to display on a user interface the manual ordered fill list.

Figure 8A:
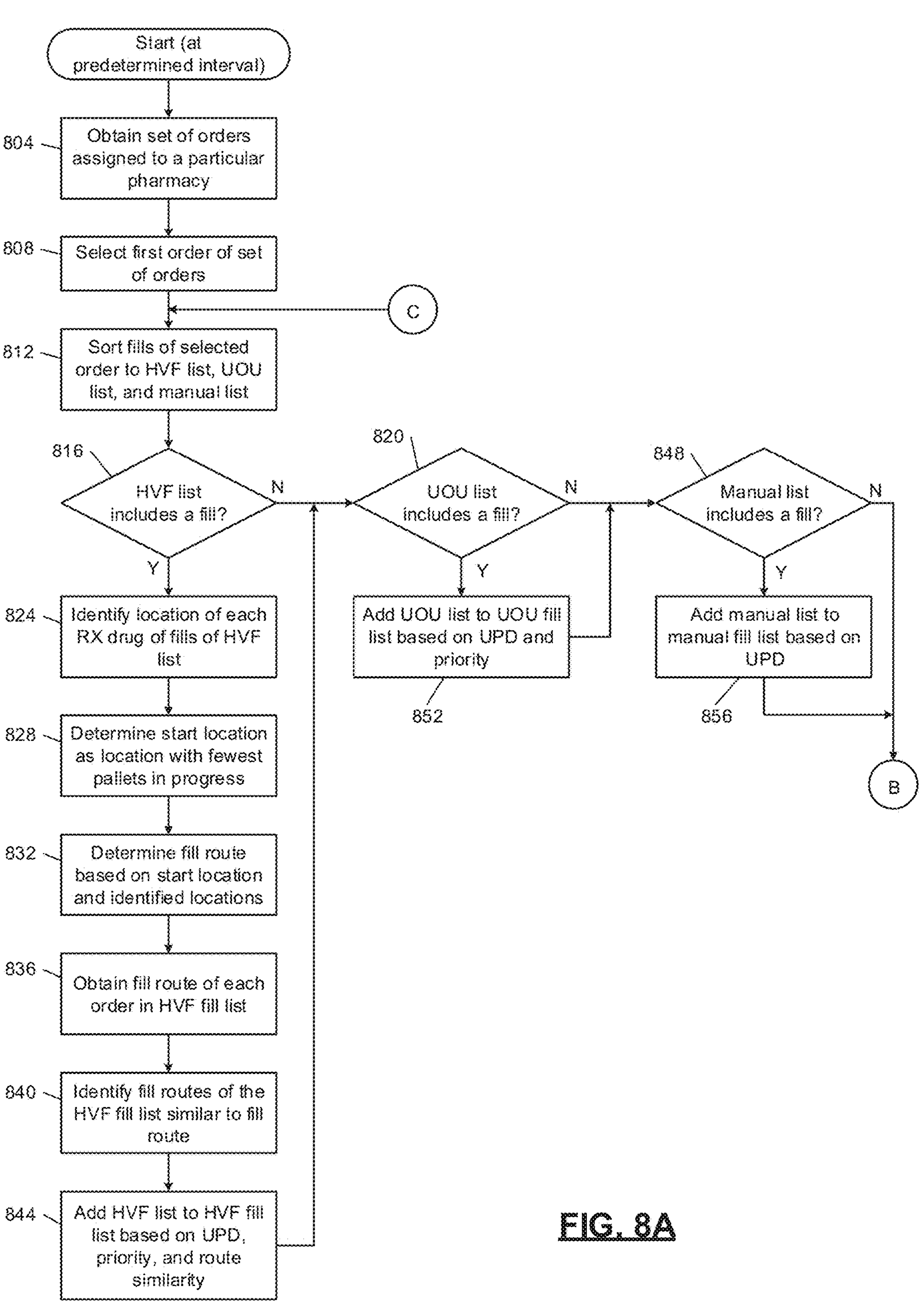
FIGS. 8A and 8B together are a flowchart of example determination of fill priority of orders routed to a pharmacy.
Figure 8B:
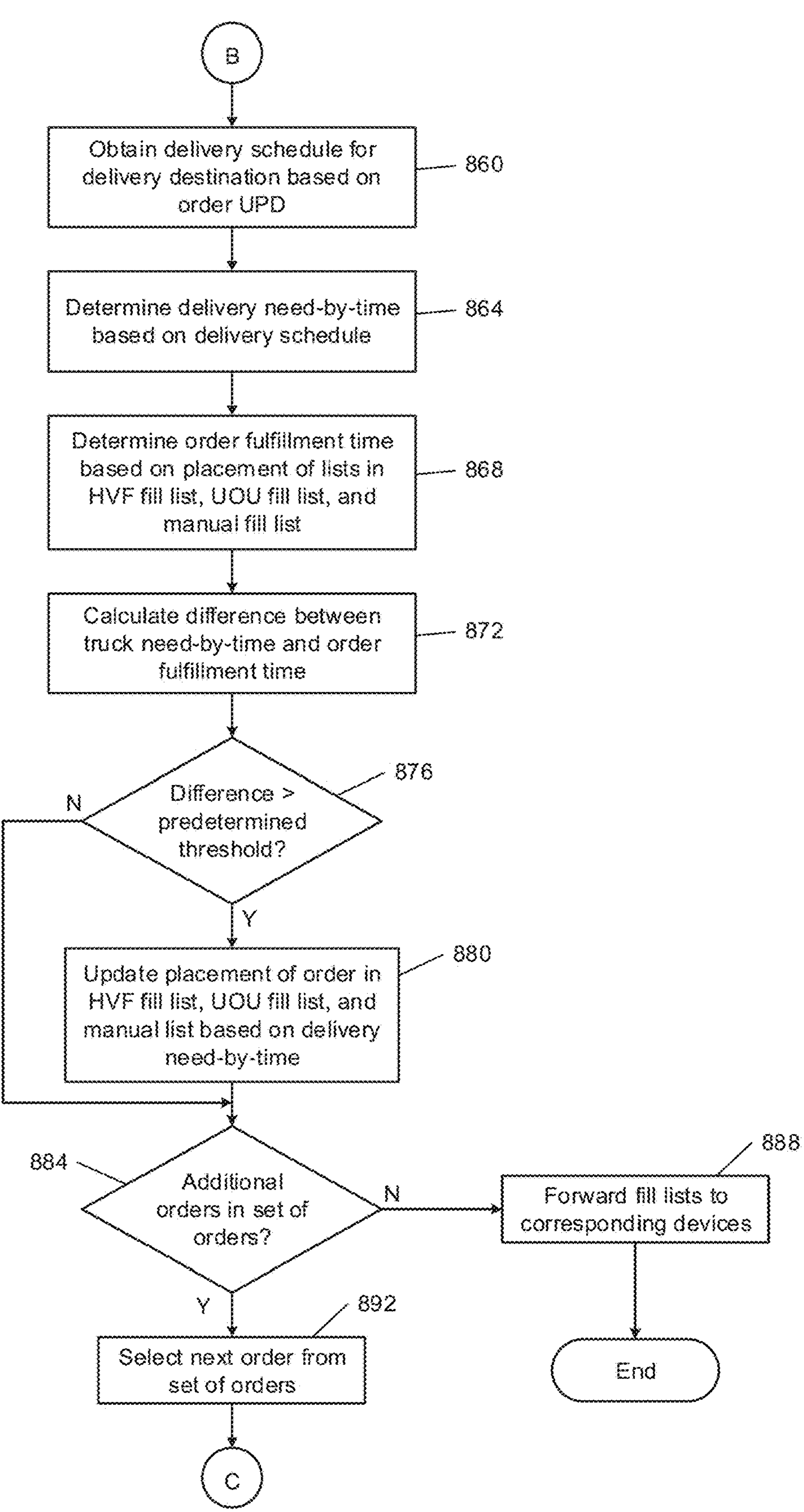

FIGS. 8A and 8B illustrate flowcharts of example determination of fill priority of orders routed to a pharmacy. In FIG. 8A, control begins at predetermined intervals, for example, prior to order fulfillment at the beginning of each day. At 804, control obtains a set of orders assigned to a particular pharmacy. Control continues to 808 to select a first order of the set of orders. Then, control proceeds to 812 to sort the fills of the selected ordered into an HVF list, UOU list, and a manual list based on a device type performing the fill. For example, each fill being performed by the HVF device is included in the HVF list, each fill being performed by the UOU device is included in the UOU list, and each fill being manually performed is included in the manual list. Once sorted, at 816, control determines if the HVF includes a fill. If no, control continues to determine if the UOU list includes a fill at 820. Otherwise, control proceeds to 824 to identify a location of each RX drug of the fills included in the HVF list in the pharmacy. Then, control continues to 828 to determine a start location as a location of the identified locations with the fewest number of pallets in progress. That is, control determines the beginning or start location of the HVF device route to fill a pallet with each fill on the HVF list.

For example, during order fulfillment, when a physical pallet is available, order vials are created and written to a selected pallet. Then, various dynamic configurable attributes are used to tune induction or fulfillment process without stopping processing or fulfillment. Additional considerations when selecting a route and selecting a pallet are the number of vials per national drug code (NDC) in order to speed up pallet time counting while under a tower. For example, as described above, when identifying a similar route, similar fills are identified so that multiple vials in a pallet of the same RX drug can be filled simultaneously. Further, a number of empty spots in a pallet are considered to determine whether the determined route is efficient.

For example, to increase speed and balance, an HVF list may be removed from the HVF fill list and is no longer filler by the HVF device (that is, control decides to not build a virtual pallet) because too many spots are empty or the number of orders is too low. The virtual pallet is a pallet created by control to implement filling and determine the route, the number of spots taken in the pallet, and the location of the HVF device at a given time. Therefore, a virtual pallet may be recycled and the filling of the HVF list may be reassigned if a predetermined time has elapsed and the virtual pallet has an insufficient number of vials.

Returning to 828, once control determines a start location, control proceeds to 832 to determine a fill route based on the start location and the identified locations as well as virtual pallet creation considerations described above. Then, control proceeds to 836 to obtain the fill routes of each order in an HVF fill list, including the set of orders that have already been processed for the HVF device. Control proceeds to 840 to identify fill routes of the HVF fill list similar to present fill route. Control continues to 844 to add the present order HVF list to the HVF fill list based on the order UPD, order priority, and route similarity (for example, the travelled distance consideration described above). In various implementations, control may determine a start time for the HVF list based on the order UPD and the order priority. The start time would be a time at which the HVF device should start fulfillment of the HVF list to meet the order UPD. Then, the HVF list is added to the HVF fill list according to the start time and route similarity, preferring an earlier start time when routes are similar.

Then, control continues to 820 to determine if the UOU list includes a fill. If no, control proceeds to 848 to determine if the manual list includes a fill. Otherwise, control continues to 852 to add the UOU list to a UOU fill list based on the order UPD and order priority. As mentioned above, in various implementations, control may determine a start time of the UOU list based on the order UPD and order priority. The start time would be a time at which the UOU device should start fulfillment of the UOU list to meet the order UPD. Then, the UOU list would be added to the UOU fill list based on the start time. Then, control proceeds to 848 to determine if the manual list includes a fill. If no, control proceeds to FIG. 8B. Otherwise, control continues to 856 to add the manual list to a manual fill list based on the order UPD, ensuring the manual list is fulfilled on time to meet the order UPD.

In FIG. 8B, control updates the HVF fill list, the UOU fill list, and the manual fill list based on delivery schedules. In various implementations, control may first process each order in the set of orders to generate the complete HVF, UOU, and manual fill lists prior to updating the lists based on delivery schedules. Then, control would update the lists for each order of the set of orders based on the delivery schedules, as shown in FIG. 8B. At 860, control obtains a delivery schedule based on the delivery destination of the corresponding order based on the order UPD.

Then, control proceeds to 864 to determine delivery need-by-time based on the delivery schedule. Then, control continues to 868 to determine an order fulfillment time based on placement of the corresponding list in the HVF fill list, the UOU fill list, and the manual fill list. That is, control determines when the entire order would be fulfilled according to the present HVF fill list, the present UOU fill list, and the present manual fill list.

At 872, control calculates a difference between the delivery need-by-time and the order fulfillment time. Then, at 876, control determines if the difference is greater than a predetermined threshold, such as one hour. That is, control determines if the estimated order fulfillment time based on the present filling order of each filling device is at least one hour prior to the delivery need-by-time (the time at which the order needs to be ready for delivery based on the delivery schedule). If the difference is less than the predetermined threshold, control continues to 880 to update placement of the lists in the HVF fill list, UOU fill list, and manual list based on the delivery need-by-time. Then, control proceeds to 884. Otherwise, if at 876 control determines the difference is greater than the predetermined threshold, control continues directly to 884. Then, control determines if additional orders are in the set of orders. If no, control proceeds to 888 and forwards the fill lists to the corresponding fill devices and control ends. Otherwise, control proceeds to 892 to select a next order from the set of orders and returns to 812 of FIG. 8A.

Figure 9:
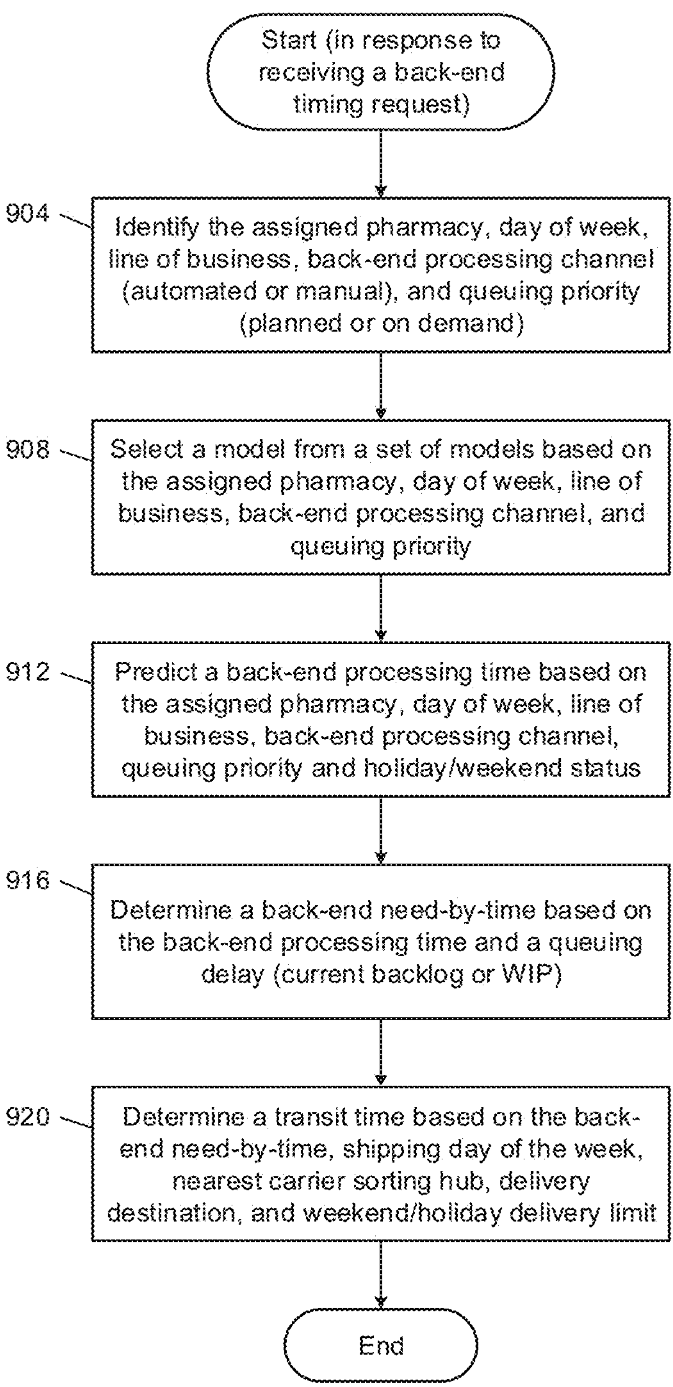
FIG. 9 is a flowchart of example back-end determination of a back-end need-by time and transit time of an order.

FIG. 9 is a flowchart illustrating example determination of a back-end need-by time and transit time of an order. Control begins in response to receiving a back-end timing request. As described above, the back-end timing request includes an individual front-end need-by time of a selected fill as well as fill parameters of the selected fill. The front-end need-by time is an estimate of when the selected fill will be ready for fulfillment by the back-end (pharmacy). The back-end timing request is a request for the back-end need-by time and the transit time of the selected fill. Then, the UPD is determined, as described in FIG. 5B, based on the front-end need-by time, the back-end need-by time, and the transit time.

Once the back-end timing request is received, control begins at 904 to identify, from the front-end need-by time and the fill parameters of the selected fill, the assigned pharmacy, a day of the week of the back-end intake, a line of business, a back-end processing channel, and a queueing prioritization (such as planned or on demand). The day of the week of the back-end intake is based on the front-end need-by time, representing which day of the week the back-end system will receive the selected fill for back-end processing, after the front-end processing has completed. In various implementations, the day of the week may indicate whether the day is a week day or a weekend day. The line of business may indicate one or both of a categorization of the selected fill and an insurance and carrier type of the selected fill. The categorization may be based on an identifier, such as National Drug Code (NDC), of the prescription drug. The NDC may indicate the back-end processing channel (such as an automated processing channel, a manual processing channel, a control processing channel or an ice processing channel).

In various implementations, the back-end system may include one or more back-end processing channels, which complete prescription drug fills using different fill techniques. For example, a manual processing channel may include unit of use processing such as filling using boxed prescription drugs, bottle prescription drugs, or bubble packed prescription drugs. An ice processing channel may include medication that is temperature sensitive and requires special processing such as coolers or larger containers to accommodate the medication, and appropriate cool packs or ice packs to keep the medication cold until it reaches its destination location. Prescription drug that use the ice processing channel may not be shipped every day of the week, and may use a different carrier than other prescription drug fills. Different models may be used to represent ice processing channel fills, using a different behavioral profile that takes into account one or more of the special features of ice processing channel fills. In various implementations, seasonality may be taken into account to determine how many packing supplies are need (for example, more ice packs are needed during warmer times of the year).

An automated processing channel may use a high volume filler and an automated packaging process, with little or no human involvement in the fill processing loop. A control processing channel may include a specific behavioral flow such as, for example, requiring a pharmacist review during fill processing, which may different from other manual processing channels.

In various implementations, the queuing priority may indicate whether or not an order has received front-end processing. A planned order type may be delayed longer than an on-demand order type. Prioritization logic may add a longer look-up table delay for the back-end processing for planned order types. For example, if a planned order type and an on-demand order type are received at the same time, the prioritization logic may add an additional twenty-four hours (or more or less) to the planned order to force the planned order further down in the backlog. The additional time may be added by adjusting a need-by-time of the planned order. In various implementations, different predictive operations may be used for on demand orders and planned orders, such as pushing back planned orders if many on-demand orders have been received recently or are in the queue.

Figure 10:
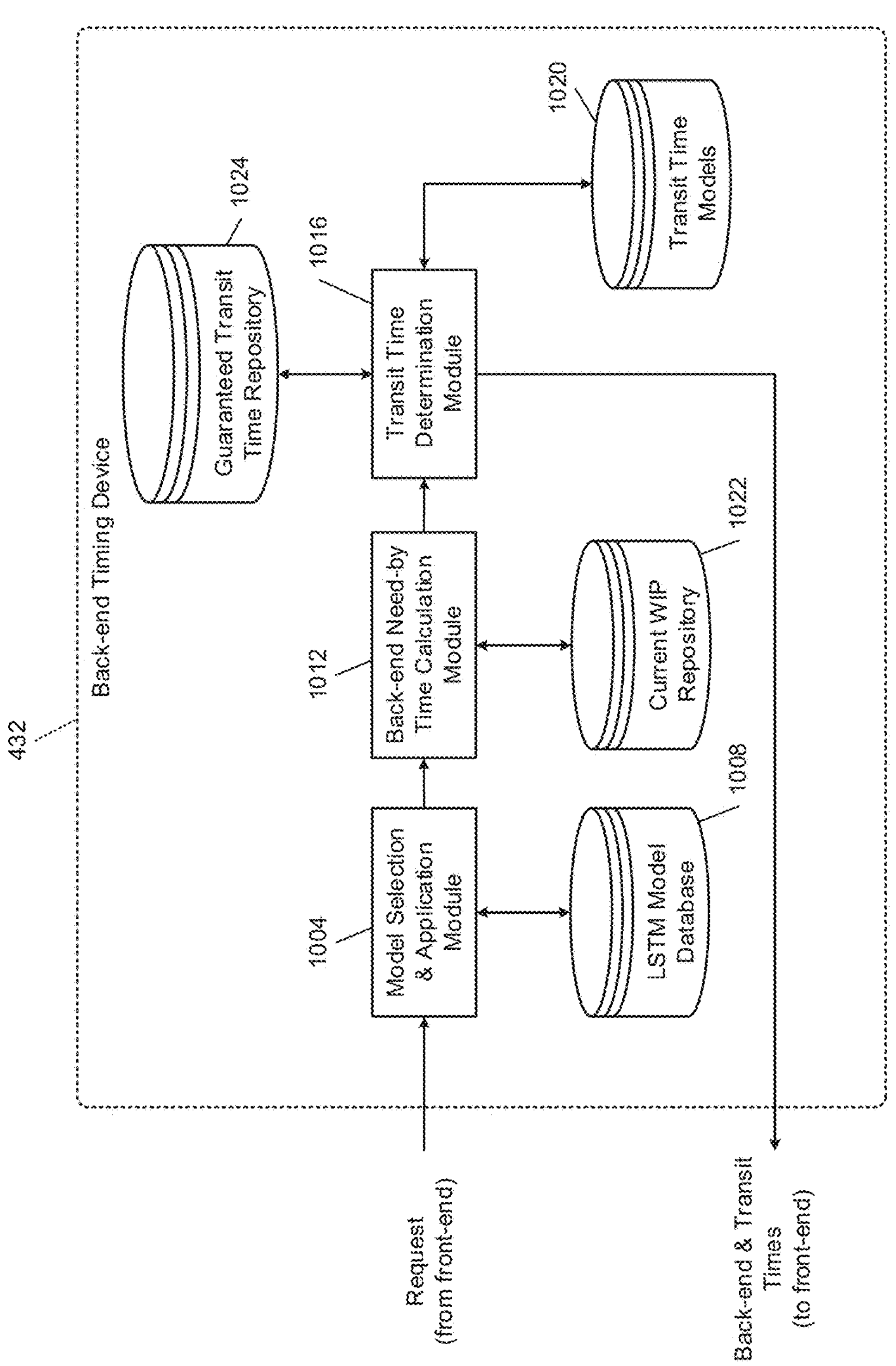
FIG. 10 is a functional block diagram of an example back-end timing device of a back-end determination system.

As described in more detail with respect to FIG. 10, each of a set of long short-term memory (LSTM) models is trained according to one or more of different lines of business, days of the week, assigned pharmacies, and back-end process channels, and queuing prioritization. In various implementations, a unique LSTM model may be trained for each unique combination of line of business, day of the week, assigned pharmacy, back-end process channel, and queuing prioritization.

The LSTM models are trained using a training dataset of historical back-end processing times. In various implementations, the LSTM models can also be trained to include a transit time in the back-end processing time to output a predicted amount of time for both completion of the back-end processes and transit to the delivery destination. The LSTM models may be updated periodically or intermittently based on additional data to fine tune the models.

At 908, control selects a first model from the set of models (the LSTM models) based on one or more variables including assigned pharmacy, day of week, line of business, back-end process channel, and queuing prioritization. In various implementations, the model selection may be primarily based on the line of business and the assigned pharmacy, or primarily based on the back-end process channel. Different models may be selected if the back-end process channel is an automated fill, if the back-end process channel is a manual fill, and so on. For example, manual fill models may offset a predicted back-end processing time or transit time by a day (or more or less) when an initial date is a weekend or holiday, while a different automated fill model may not include the same weekend and holiday offsets.

Control continues to 912 to predict the back-end timing using the selected model. For example, if the model is selected based on line of business, then the selected model can predict the back-end timing based on inputs including the assigned pharmacy, the day of the week, the process channel, and weekends and holidays. If an initial date is a weekend, a Sunday, or a holiday, the predicted back-end timing may be offset by a day (or more or less time).

As mentioned previously, the back-end timing may include the transit time. When the back-end timing includes the transit time, the selected model may use additional variables, such as a delivery destination and carrier sorting hub, to determine the back-end timing. Otherwise, if the transit time is determined separately, the back-end timing indicates an amount of processing time needed by the back-end system. Then, at 916, control determines a back-end need-by time based on the front-end need-by time, the back-end timing, and the queueing delay based on the current backlog or Work in Progress (WIP), indicating a time at which the selected fill is prepared for transit.

For example, control may determine a current backlog of orders waiting to be filled, or a current amount of WIP orders, in order to determine whether the backlog may affect the predicted time at which the selected fill will be prepared for transit. In various implementations, control may compare the backlog or WIP to a specified threshold, such as double or triple a normal baseline level, and add a delay impact on the predicted time when the backlog or WIP exceeds the threshold. For example, control add one day to the predicted time when the backlog exceeds double the normal baseline level, control may add two days to the predicted time when the backlog exceeds triple the normal baseline level, and so on.

Then, control continues to 920 to determine the transit time. For example, control may determine the transit time based on the back-end need-by time, the shipping day of the week, the carrier sorting hub, the delivery destination, and weekend and holiday limits on delivery days. In various implementations, control may also use the nearest available carrier truck pickup time. Control may use these as inputs to one or both of a trained model (such as a random forest model) and a lookup table. As one example, a lookup table may include a transit schedule with carrier provided guaranteed transport times and locations. Based on the transit schedule, control can estimate a transit time to the delivery destination using the back-end need-by time as the time when the fill is prepared for delivery. As discussed with respect to FIG. 5B, the latest individual back-end need-by time is selected as the order need-by time, which also selects the latest transit time. In various implementations, control forwards the transit time and the back-end need-by time to the front-end system. Then, control ends.

Back-End Timing Device

FIG. 10 illustrates a functional block diagram of an example back-end timing device 432 of a back-end determination system. As briefly discussed above, the back-end timing device 432 implements a machine learning algorithm to estimate back-end timing or a back-end processing time of the back-end system described in FIG. 4. The back-end timing device 432 determines the back-end need-by time based on the estimated back-end timing. In various implementations, the back-end timing device 432 may also implement machine learning algorithms to estimate a transit time of a selected fill to reach a delivery destination.

The back-end timing device 432 includes a model selection and application module 1004. The model selection and application module 1004 receives, from the front-end determination system 404 of FIG. 4, a request for the back-end need-by time and the transit time of a selected fill. The request includes the front-end need-by time, indicating when the back-end would receive the selected fill for processing, and the fill parameters, including an assigned pharmacy, RX drug, etc. The model selection and application module 1004 identifies a line of business of the selected fill according to fill parameters, such as RX drug, insurance information, etc. In various implementations, the line of business is included in the fill parameters of the selected fill.

The model selection and application module 1004 selects an LSTM model from an LSTM model database 1008 based on at least one of the line of business, the assigned pharmacy, the day of the week of back-end intake (that is, the day of the week the back-end would receive the selected fill for processing), the back-end processing channel for the given NDC, and a queuing prioritization. The LSTM model database 1008 stores a plurality of LSTM models trained using training datasets. Each LSTM model of the plurality of LSTM models may be trained for a particular line of business using training data for the particular line of business. In various implementations, the LSTM model database 1008 may include front-end machine learning models trained to predict a front-end time associated with a fill, or transit time machine learning models trained to predict a transit time associated with a fill.

Each LSTM is trained to predict the amount of back-end time (back-end timing) the back-end system needs to complete back-end processes. Variables affecting the back-end timing may include the day of the week the back-end receives the selected fill as well as the assigned pharmacy for the selected fill, independent of the line of business. The LSTM models are trained using the training data and fine-tuned using the presently selected predictions.

In various implementations, the LSTM models may also predict the transit time of the selected fill based on the delivery destination. The same LSTM models may be used to determine an overall timing including the back-end timing of the back-end system and transit time. In various implementations, a separate set of LSTM models may be trained to predict transit times based on delivery destinations (for example, based on distance from the assigned pharmacy) and the back-end need-by time (the time when the back-end is predicted to complete processing the selected fill), the shipped day of the week, and the predicted delivery day of the week. In various implementations, the transit time may be a set amount of time based on a delivery distance, day of week, carrier schedule, or regional factors.

For example, the model selection and application module 1004 selects a first LSTM model from the LSTM model database 1008 and uses the first LSTM model to estimate a back-end timing representing an amount of time the back-end system will need to process the selected fill. The back-end timing is forwarded to a back-end need-by time calculation module 1012. The back-end need-by time calculation module 1012 calculates a back-end need-by time indicating when the back-end system completes back-end processing of the selected fill from the received front-end need-by time (the estimated time the front-end processing will be completed) and the estimated back-end timing.

The back-end need-by time calculation module 1012 forwards the back-end need-by time to a transit time determination module 1016. The transit time determination module 1016 obtains, from the fill parameters, the delivery destination. The transit time determination module 1016 determines a distance between the delivery destination and the assigned pharmacy. The transit time determination module 1016 accesses a transit time database 1020 that indicates, based on the distance, an estimated transit time. As described above, the transit time database 1020 may alternatively indicate a transit schedule, from which the transit time determination module 1016 can identify a scheduled delivery truck the selected fill will be completed for (based on the back-end need-by time) and determine, according to the schedule of the scheduled delivery truck, when the selected fill would reach the delivery destination. The transit time determination module 1016 then forwards the back-end need-by time and the transit time to the front-end determination system 404 of FIG. 4.

In various implementations, the transit time database 1020 may include one or more models to predict the transit time. For example, a machine learning algorithm such as a decision tree based random forest model may be used to predict the transit time, based on a day of shipping, a location and capacity of the nearest carrier hub, and so on.

The back-end timing device 432 optionally includes a guaranteed transit time repository 1024 (or obtains data from an external guaranteed transit time repository provided by a carrier). For example, a carrier such as DHL may supply guaranteed transit times for various distances, locations, dates, times, delivery destinations, package sizes, and so on. The transit time determination module 1016 may obtain a guaranteed transit time value from the guaranteed transit time repository 1024 according to parameters of the order to be filled, and use the obtained value alone, or in combination with a predictive model from the transit time database 1020, to determine a transit time for the order to be filled.

As shown in FIG. 10, the back-end timing device 432 may include an optional current WIP repository 1022 (sometimes referred to as a queue repository). The current WIP repository 1022 may store data indicative of a current backlog or WIP value (such as a daily amount of orders that are waiting to be filled or currently being filled by the system). The back-end need-by-time calculation module 1012 may obtain the current backlog or WIP value from the current WIP repository 1022, for determination of a predicted fill time of an order. As explained above, the back-end-timing device 432 may adjust a predicted fill time when a backlog or WIP value exceeds a specified threshold.

Machine-Learning Models

Figures 11A, 11B:
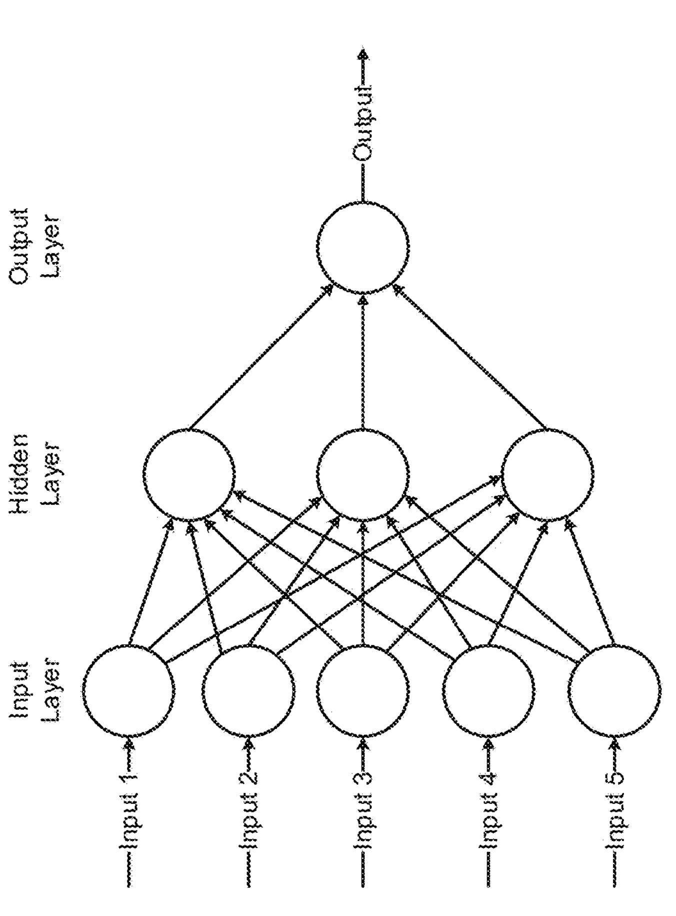
FIGS. 11A and 11B are graphical representations of an example recurrent neural network to implement machine learning models.

The machine learning models used by the back-end timing device 432 (or the front-end timing device 420) may take the form of a recurrent neural network (RNN), such as a long short-term memory (LSTM) model. FIGS. 11A and 11B illustrate an example RNN. Machine learning is a method used to devise complex models and algorithms that lend themselves to prediction (e.g., health plan customer predictions, etc.). The models generated using machine learning can produce reliable, repeatable decisions and results, and uncover hidden insights through learning from historical relationships and trends in the data.

The purpose of using the recurrent-neural-network-based model and training the model using machine learning as described above is to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 11A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 11B). In the input layer, the number of neurons equals number of features (columns) in a dataset. The output layer can have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes that would not noticeably affect network performance may be removed from the network during training. For example, nodes with weights approaching zero after training can be removed (this process is called pruning). The number of neurons can cause under-fitting (inability to adequately capture signals in dataset) or over-fitting (insufficient information to train all neurons; network performs well on training dataset but not on test dataset).

Various methods and criteria can be used to measure performance of a neural network model (for example, by the model selection and application module 1004). For example, root mean squared error (RMSE) measures the average distance between observed values and model predictions. Coefficient of Determination ($R^2$) measures correlation (not accuracy) between observed and predicted outcomes (for example, between trained model outputs and actual outputs of test data). This method may not be reliable if the data has a large variance. Other performance measures include irreducible noise, model bias, and model variance. A high model bias for a model indicates that the model is not able to capture true relationship between predictors and the outcome. Model variance can indicate whether a model is not stable (a slight perturbation in the data will significantly change the model fit).

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system for transforming a user interface according to a plurality of machine learning models, the computer system comprising:

a data store configured to store an order, wherein the order specifies a set of fills and fill parameters for each fill of the set of fills;

an automatic fulfillment device configured to:

receive the set of fills and the fill parameters for each fill of the set of fills;

determine a set of locations of a set of medications, wherein:

each medication of the set of medications is associated with at least one location of the set of locations, each medication of the set of medications is associated with at least one fill of the set of fills, and the set of locations are within a medication storage area;

determine a route through the medication storage area based on each location in the set of locations; and automatically complete the set of fills by traversing the route without operator intervention;

a back-end timing circuit configured to, for each fill of the set of fills:

receive a front-end time and the fill parameters for the fill, wherein the front-end time is based on a front-end delay that indicates an amount of time to complete a set of pre-fulfillment tasks for the fill;

determine, based on at least one of the fill parameters and the front-end time, a set of model selection parameters including at least one of an assigned pharmacy of the fill, a parameter associated with the automatic fulfillment device, a line of business of the fill, a time that a back-end system will receive the fill, a back-end processing channel for the fill, and a queuing priority of the fill;

select one of the plurality of machine learning models based on at least a portion of the set of model selection parameters;

supply at least a portion of the set of model selection parameters to the selected machine learning model to generate a prediction of a back-end time corresponding to the fill, wherein the back-end time indicates an amount of time to complete a set of back-end processes to prepare the fill for shipping; and determine a transit time, wherein the transit time corresponds to physical delivery of the fill to an address of a user;

a user promise date circuit configured to:

for each fill of the set of fills, calculate a fill promise date based on (i) the back-end time for the fill and (ii) the transit time for the fill, and select a latest one of the fill promise dates as a user promise date; and a notification circuit configured to selectively transform the user interface based on the user promise date.

2. The system of claim 1 wherein the back-end timing circuit is configured to, for each fill of the set of fills:

select a transit time machine learning model from the plurality of machine learning models; and determine the transit time according to a prediction output of the selected transit time machine learning model.

3. The system of claim 2 wherein the back-end timing circuit is configured to:

obtain a queuing delay value according to at least one of a current backlog of the back-end system and a current work in progress (WIP) of the back-end system; and for each fill of the set of fills, determine a back-end completion time according to the queuing delay value and the back-end time corresponding to the fill, wherein the back-end completion time indicates a time when the set of back-end processes will be completed.

4. The system of claim 3 wherein the back-end timing circuit is configured to, for each fill of the set of fills:

identify one or more transit parameters of the fill including at least one of the queuing delay value, a day of the week that the fill will be shipped, a nearest carrier sorting hub to a location of the assigned pharmacy of the fill, a delivery destination of the fill, and a weekend or holiday delivery status associated with the day that the fill will be shipped; and supply the one or more transit parameters as input to the selected transit time machine learning model to generate the prediction output.

5. The system of claim 3 wherein:

the back-end timing circuit includes a queue repository configured to store data indicative of the current backlog of the back-end system or the current work in progress (WIP) of the back-end system; and the back-end timing circuit is configured to:

obtain the queuing delay value from the queue repository;

compare the queuing delay value to a specified threshold; and for each fill in the set of fills, increase the back-end time corresponding to the fill in response to the queuing delay value exceeding the specified threshold.

6. The system of claim 2 wherein the transit time machine learning model comprises a decision tree based random forest model.

7. The system of claim 1 wherein the back-end timing circuit is configured to, for each fill of the set of fills:

access a guaranteed delivery time repository, wherein the guaranteed delivery time repository is associated with at least one delivery carrier and stores data indicative of guaranteed delivery time values provided by the delivery carrier; and determine the transit time for the fill by looking up a guaranteed delivery time value from the guaranteed delivery time repository according to a time of shipping the fill.

8. The system of claim 1 wherein:

the queuing priority of each fill includes a planned fill status or an on-demand fill status; and the back-end timing circuit is configured to increase the back-end time for each fill of the set of fills having the planned fill status.

9. The system of claim 1 further comprising a front-end timing circuit configured to, for each fill of the set of fills:

select a front-end machine learning model from the plurality of machine learning models; and determine the front-end time corresponding to the fill according to a prediction output of the selected front-end machine learning model.

10. The system of claim 1 further comprising a front-end timing circuit, wherein:

the back-end timing circuit is configured to select a latest one of the back-end times for the set of fills as an order back-end time; and the front-end timing circuit is configured to:

from the front-end times for each fill of the set of fills, select a latest one of the front-end times as an order front-end time;

determine a latest time the order could be transmitted to a back-end system while maintaining the order back-end time; and adjust the order front-end time based on the determined latest time.

11. The system of claim 1 wherein the transformation of the user interface includes displaying the user promise date on at least one of a web portal and a mobile application.

12. The system of claim 1 further comprising a front-end timing circuit and a plurality of lookup tables corresponding to pre-fulfillment tasks, wherein the front-end timing circuit is configured to determine the front-end delay of a first fill of the set of fills by, for each task in the set of pre-fulfillment tasks for the first fill:

identifying a lookup table of the plurality of lookup tables corresponding to the task;

selecting a value from the identified lookup table; and updating the front-end delay based on the selected value.

13. The system of claim 1 further comprising:

a split circuit configured to split the order into a set of sub-orders in response to at least one fill of the set of fills being assigned to a different pharmacy from at least one other fill of the set of fills; and a router circuit configured to route each sub-order of the set of sub-orders to the respective pharmacy assignment.

14. The system of claim 1 wherein:

the assigned pharmacy of a first fill of the set of fills is based on (i) a distance between the assigned pharmacy and a destination associated with the order, (ii) a stock of a drug associated with the first fill at the assigned pharmacy, and (iii) whether the drug associated with the first fill is a controlled substance, and the fill parameters for the first fill of the set of fills include (i) a drug identifier indicating a drug for the first fill, (ii) a prescribed strength of the drug, (iii) a prescribed quantity of the drug, and (iv) a controlled substance status of the drug.

15. The system of claim 1 further comprising:

a pharmacy assignment circuit configured to receive the order from the data store and, for each fill of the set of fills, determine the assigned pharmacy for the fill according to the fill parameters of the fill; and a front-end timing circuit configured to, for each fill of the set of fills, determine the front-end time corresponding to the fill.

16. The system of claim 1 wherein the time is a calendar date, and the fill parameters include a day of the week that the back-end system will receive the fill.

17. A computer system for transforming a user interface according to a plurality of machine learning models, the computer system comprising:

memory hardware configured to store computer-executable instructions and an order, wherein the order specifies a set of fills and fill parameters for each fill of the set of fills; and processor hardware configured to execute the instructions, wherein the instructions include:

receiving the set of fills and the fill parameters for each fill of the set of fills;

determining a set of locations of a set of medications, wherein:

each medication of the set of medications is associated with at least one location of the set of locations, each medication of the set of medications is associated with at least one fill of the set of fills, and the set of locations are within a medication storage area;

determining a route for an automatic fulfillment device through the medication storage area based on each location in the set of locations;

automatically completing, via the automatic fulfillment device, the set of fills by traversing the route without operator intervention;

for each fill of the set of fills:

receiving a front-end time and the fill parameters for the fill, wherein the front-end time is based on a front-end delay that indicates an amount of time to complete a set of pre-fulfillment tasks for the fill;

determining, based on at least one of the fill parameters and the front-end time, a set of model selection parameters including at least one of an assigned pharmacy of the fill, a parameter associated with the automatic fulfillment device, a line of business of the fill, a time that a back-end system will receive the fill, a back-end processing channel for the fill, and a queuing priority of the fill;

selecting one of the plurality of machine learning models based on at least a portion of the set of model selection parameters;

supplying at least a portion of the set of model selection parameters to the selected machine learning model to generate a prediction of a back-end time corresponding to the fill, wherein the back-end time indicates an amount of time to complete a set of back-end processes to prepare the fill for shipping;

determining a transit time, wherein the transit time corresponds to physical delivery of the fill to an address of a user; and calculating a fill promise date based on (i) the back-end time for the fill and (ii) the transit time for the fill;

selecting a latest one of the fill promise dates as a user promise date; and selectively transforming the user interface based on the user promise date.

18. A computerized method of transforming a user interface according to a plurality of machine learning models, the method comprising:

receiving a set of fills specified by an order, wherein each fill of the set of fills includes fill parameters;

determining a set of locations of a set of medications, wherein:

each medication of the set of medications is associated with at least one location of the set of locations, each medication of the set of medications is associated with at least one fill of the set of fills, and the set of locations are within a medication storage area;

determining a route for an automatic fulfillment device through the medication storage area based on each location in the set of locations;

automatically completing, via the automatic fulfillment device, the set of fills by traversing the route without operator intervention;

for each fill of the set of fills:

receiving a front-end time and the fill parameters for the fill, wherein the front-end time is based on a front-end delay that indicates an amount of time to complete a set of pre-fulfillment tasks for the fill;

determining, based on at least one of the fill parameters and the front-end time, a set of model selection parameters including at least one of an assigned pharmacy of the fill, a parameter associated with the automatic fulfillment device, a line of business of the fill, a time that a back-end system will receive the fill, a back-end processing channel for the fill, and a queuing priority of the fill;

selecting one of the plurality of machine learning models based on at least a portion of the set of model selection parameters;

supplying at least a portion of the set of model selection parameters to the selected machine learning model to generate a prediction of a back-end time corresponding to the fill, wherein the back-end time indicates an amount of time to complete a set of back-end processes to prepare the fill for shipping;

determining a transit time, wherein the transit time corresponds to physical delivery of the fill to an address of a user; and calculating a fill promise date based on (i) the back-end time for the fill and (ii) the transit time for the fill;

selecting a latest one of the fill promise dates as a user promise date; and selectively producing a modification of the user interface based on the user promise date.

19. The method of claim 18, further comprising, for each fill of the set of fills:

selecting a transit time machine learning model from the plurality of machine learning models; and determining the transit time according to a prediction output of the selected transit time machine learning model.

20. The method of claim 19, further comprising;

obtaining a queuing delay value according to at least one of a current backlog of the back-end system and a current work in progress (WIP) of the back-end system; and for each fill of the set of fills, determining a back-end completion time according to the queuing delay value and the back-end time corresponding to the fill, wherein the back-end completion time indicates a time when the set of back-end processes will be completed.

21. The method of claim 18, wherein the route is based on at least one of:

a distance travelled by the automatic fill device, or a wait time at each location of the set of locations.

22. The system of claim 1, wherein the route is based on at least one of:

a distance travelled by the automatic fill device, or a wait time at each location of the set of locations.

23. The system of claim 17, wherein the route is based on at least one of:

a distance travelled by the automatic fill device, or a wait time at each location of the set of locations.

* * * * *